US010458605B2

(12) United States Patent
Ting et al.

(10) Patent No.: US 10,458,605 B2
(45) Date of Patent: Oct. 29, 2019

(54) LIGHT SOURCE MODULE

(71) Applicants: NATIONAL CHUNG CHENG UNIVERSITY, Chiayi County (TW); SANDASTER INTERNATIONAL LTD., Tainan (TW)

(72) Inventors: Chu-Chi Ting, Chiayi County (TW); Yu-Wen Huang, Tainan (TW)

(73) Assignees: NATIONAL CHUNG CHENG UNIVERSITY, Minxiong Township, Chiayi County (TW); SANDASTER INTERNATIONAL LTD., Tainan (TW)

( * ) Notice: Subject to any disclaimer, the term of this patent is extended or adjusted under 35 U.S.C. 154(b) by 73 days.

(21) Appl. No.: 15/354,336

(22) Filed: Nov. 17, 2016

(65) Prior Publication Data

US 2017/0343168 A1 Nov. 30, 2017

(30) Foreign Application Priority Data

May 25, 2016 (TW) .............................. 105116261 A

(51) Int. Cl.
*F21K 9/64* (2016.01)
*F21S 10/00* (2006.01)
(Continued)

(52) U.S. Cl.
CPC ................ *F21K 9/64* (2016.08); *A01G 33/00* (2013.01); *A01H 3/02* (2013.01); *F21S 10/00* (2013.01);
(Continued)

(58) Field of Classification Search
CPC .......... A01G 7/045; A01G 33/00; A01H 3/02; F21Y 2113/13; F21Y 2113/17;
(Continued)

(56) References Cited

U.S. PATENT DOCUMENTS 8,549,787 B2   10/2013   Aikala
8,944,631 B2   2/2015   Pan et al.
(Continued)

FOREIGN PATENT DOCUMENTS

CN   201746536 U   2/2011
CN   204168547 U   2/2015
(Continued)

*Primary Examiner* — Zheng Song
(74) *Attorney, Agent, or Firm* — Muncy, Geissler, Olds & Lowe, PC

(57) ABSTRACT

A light source module includes a wiring board and a LED array electrically connected to the wiring board. The LED array can be driven to emit a first group of emission peaks in 300 nm≤$\lambda_{max}$<450 nm, a second group of emission peaks in 450 nm≤$\lambda_{max}$<550 nm, and a third group of emission peaks in 550 nm for matching the spectrum of sunlight underwater. When the maximum peak intensity of the emission peaks in the second group is taken as 1.0, the peak intensity $I_a$ of each emission peak in the first group is in a range of 0<$I_a$≤0.9, and the peak intensity $I_b$ of each emission peak in the third group is in a range of 0<$I_b$≤0.9. Accordingly, the light source module is suitable for aquatic species and can enhance growing rate of the aquatic species.

17 Claims, 33 Drawing Sheets

(51) Int. Cl.
*F21V 19/00* (2006.01)
*H01L 33/48* (2010.01)
*H01L 33/50* (2010.01)
*H01L 33/54* (2010.01)
*H01L 33/62* (2010.01)
*H05B 33/08* (2006.01)
*A01G 33/00* (2006.01)
*A01H 3/02* (2006.01)
*F21Y 113/13* (2016.01)
*F21Y 115/10* (2016.01)
*A01G 7/04* (2006.01)
*C12M 1/00* (2006.01)

(52) U.S. Cl.
CPC ........ *F21V 19/0025* (2013.01); *H01L 33/486* (2013.01); *H01L 33/502* (2013.01); *H01L 33/54* (2013.01); *H01L 33/62* (2013.01); *H05B 33/0845* (2013.01); *A01G 7/045* (2013.01); *C12M 31/10* (2013.01); *C12M 41/06* (2013.01); *F21Y 2113/13* (2016.08); *F21Y 2115/10* (2016.08); *Y02P 60/149* (2015.11)

(58) Field of Classification Search
CPC ........ F21Y 2115/10; F21K 9/94; F21S 10/00; F21V 19/0025; H01L 33/502; H01L 33/54; H01L 33/62; H01L 33/486; H05B 33/0845; C12M 31/10; C12M 41/06
See application file for complete search history.

(56) References Cited

U.S. PATENT DOCUMENTS

| | | | |
|---|---|---|---|
| 2007/0223219 A1* | 9/2007 | Medendorp, Jr. | C09K 11/586 362/231 |
| 2009/0152572 A1* | 6/2009 | Su | F21K 9/00 257/89 |
| 2009/0224693 A1* | 9/2009 | Mukai | H05B 33/0821 315/295 |
| 2010/0157586 A1* | 6/2010 | Yang | F21K 9/00 362/230 |
| 2010/0264431 A1* | 10/2010 | Akutsu | H01L 33/505 257/89 |
| 2014/0191655 A1* | 7/2014 | Kasakura | H01L 25/0753 315/32 |
| 2016/0007422 A1* | 1/2016 | Zukauskas | H01L 33/50 315/294 |
| 2016/0043289 A1 | 2/2016 | Inomata et al. | |
| 2016/0178140 A1* | 6/2016 | Cho | F21V 19/0035 362/217.15 |
| 2017/0011670 A1* | 1/2017 | van de Ven | F21K 9/60 |

FOREIGN PATENT DOCUMENTS

| | | |
|---|---|---|
| EP | 2883950 A1 | 6/2015 |
| GB | 2467008 A | 7/2010 |
| JP | 2008066138 A | 3/2008 |

\* cited by examiner

| 227 | 211 | 215 | 227 | 235 | 233 | 225 | 235 | 233 | 251 |
|-----|-----|-----|-----|-----|-----|-----|-----|-----|-----|
| 217 | 231 | 221 | 251 | 219 | 229 | 251 | 217 | 231 | 225 |
| 233 | 213 | 225 | 235 | 217 | 215 | 227 | 235 | 251 | 223 |
| 235 | 231 | 229 | 233 | 225 | 251 | 211 | 225 | 233 | 229 |
| 233 | 219 | 251 | 251 | 229 | 233 | 223 | 231 | 235 | 229 |
| 213 | 225 | 235 | 233 | 227 | 231 | 251 | 233 | 219 | 251 |
| 251 | 225 | 229 | 223 | 233 | 219 | 231 | 251 | 229 | 233 |
| 225 | 233 | 223 | 213 | 225 | 235 | 233 | 225 | 223 | 229 |
| 231 | 229 | 233 | 227 | 229 | 233 | 235 | 229 | 251 | 233 |
| 223 | 251 | 229 | 235 | 233 | 227 | 231 | 233 | 211 | 225 |

FIG. 14

| 211 | 217 | 223 | 225 | 229 | 229 | 233 | 233 | 235 | 251 |
| 211 | 219 | 223 | 225 | 229 | 231 | 233 | 233 | 235 | 251 |
| 211 | 219 | 225 | 225 | 229 | 231 | 233 | 233 | 235 | 251 |
| 213 | 219 | 225 | 227 | 229 | 231 | 233 | 233 | 235 | 251 |
| 213 | 219 | 225 | 227 | 229 | 231 | 233 | 233 | 235 | 251 |
| 213 | 221 | 225 | 227 | 229 | 231 | 233 | 233 | 235 | 251 |
| 215 | 223 | 225 | 227 | 229 | 231 | 233 | 233 | 235 | 251 |
| 215 | 223 | 225 | 227 | 229 | 231 | 233 | 235 | 251 | 251 |
| 217 | 223 | 225 | 227 | 229 | 231 | 233 | 235 | 251 | 251 |
| 217 | 223 | 225 | 229 | 229 | 233 | 233 | 235 | 251 | 251 |

FIG. 16

| 211 | 217 | 223 | 225 | 227 | 229 | 229 | 231 | 233 | 233 |
|-----|-----|-----|-----|-----|-----|-----|-----|-----|-----|
| 211 | 217 | 223 | 225 | 227 | 229 | 229 | 233 | 233 | 233 |
| 211 | 219 | 223 | 225 | 227 | 229 | 231 | 233 | 233 | 235 |
| 213 | 219 | 223 | 225 | 227 | 229 | 231 | 233 | 233 | 235 |
| 213 | 219 | 223 | 225 | 227 | 229 | 231 | 233 | 233 | 235 |
| 213 | 221 | 223 | 225 | 227 | 229 | 231 | 233 | 233 | 235 |
| 215 | 221 | 225 | 225 | 229 | 229 | 231 | 233 | 233 | 235 |
| 215 | 221 | 225 | 225 | 229 | 229 | 231 | 233 | 233 | 235 |
| 217 | 221 | 225 | 225 | 229 | 229 | 231 | 233 | 233 | 235 |
| 217 | 223 | 225 | 227 | 229 | 229 | 231 | 233 | 233 | 251 |

FIG. 22

| 211 | 217 | 223 | 225 | 225 | 229 | 229 | 231 | 233 | 233 |
|-----|-----|-----|-----|-----|-----|-----|-----|-----|-----|
| 211 | 217 | 223 | 225 | 227 | 229 | 229 | 233 | 233 | 233 |
| 211 | 219 | 223 | 225 | 227 | 229 | 229 | 233 | 233 | 233 |
| 213 | 219 | 223 | 225 | 227 | 229 | 231 | 233 | 233 | 233 |
| 213 | 219 | 223 | 225 | 227 | 229 | 231 | 233 | 233 | 233 |
| 213 | 219 | 223 | 225 | 227 | 229 | 231 | 233 | 233 | 235 |
| 215 | 221 | 223 | 225 | 227 | 229 | 231 | 233 | 233 | 235 |
| 215 | 221 | 223 | 225 | 227 | 229 | 231 | 233 | 233 | 235 |
| 217 | 221 | 225 | 225 | 227 | 229 | 231 | 233 | 233 | 235 |
| 217 | 221 | 225 | 225 | 229 | 229 | 231 | 233 | 233 | 235 |

FIG. 26

| 211 | 217 | 221 | 223 | 225 | 227 | 229 | 229 | 231 | 233 |
|-----|-----|-----|-----|-----|-----|-----|-----|-----|-----|
| 211 | 217 | 221 | 223 | 225 | 227 | 229 | 229 | 233 | 233 |
| 211 | 217 | 221 | 223 | 225 | 227 | 229 | 229 | 233 | 233 |
| 213 | 219 | 223 | 225 | 225 | 227 | 229 | 231 | 233 | 233 |
| 213 | 219 | 223 | 225 | 225 | 227 | 229 | 231 | 233 | 235 |
| 213 | 219 | 223 | 225 | 225 | 227 | 229 | 231 | 233 | 235 |
| 215 | 219 | 223 | 225 | 225 | 229 | 229 | 231 | 233 | 235 |
| 215 | 219 | 223 | 225 | 225 | 229 | 229 | 231 | 233 | 251 |
| 217 | 219 | 223 | 225 | 225 | 229 | 229 | 231 | 233 | 251 |
| 217 | 221 | 223 | 225 | 227 | 229 | 229 | 231 | 233 | 251 |

FIG. 30

| 211 | 217 | 221 | 223 | 225 | 227 | 229 | 229 | 233 | 233 |
|-----|-----|-----|-----|-----|-----|-----|-----|-----|-----|
| 211 | 217 | 221 | 223 | 225 | 227 | 229 | 231 | 233 | 233 |
| 211 | 217 | 221 | 223 | 225 | 227 | 229 | 231 | 233 | 233 |
| 213 | 219 | 223 | 225 | 225 | 227 | 229 | 231 | 233 | 233 |
| 213 | 219 | 223 | 225 | 225 | 227 | 229 | 231 | 233 | 233 |
| 213 | 219 | 223 | 225 | 225 | 227 | 229 | 231 | 233 | 233 |
| 215 | 219 | 223 | 225 | 225 | 229 | 229 | 231 | 233 | 233 |
| 215 | 219 | 223 | 225 | 225 | 229 | 229 | 231 | 233 | 235 |
| 217 | 219 | 223 | 225 | 227 | 229 | 229 | 231 | 233 | 235 |
| 217 | 221 | 223 | 225 | 227 | 229 | 229 | 233 | 233 | 235 |

| 211 | 217 | 221 | 223 | 225 | 227 | 229 | 229 | 231 | 233 |
|-----|-----|-----|-----|-----|-----|-----|-----|-----|-----|
| 211 | 217 | 221 | 223 | 225 | 227 | 229 | 229 | 231 | 233 |
| 211 | 219 | 223 | 223 | 225 | 227 | 229 | 229 | 231 | 233 |
| 213 | 219 | 223 | 225 | 225 | 227 | 229 | 229 | 231 | 233 |
| 213 | 219 | 223 | 225 | 225 | 227 | 229 | 231 | 231 | 233 |
| 213 | 219 | 223 | 225 | 225 | 227 | 229 | 231 | 231 | 233 |
| 215 | 219 | 223 | 225 | 225 | 227 | 229 | 231 | 233 | 233 |
| 215 | 219 | 223 | 225 | 225 | 227 | 229 | 231 | 233 | 233 |
| 217 | 221 | 223 | 225 | 225 | 227 | 229 | 231 | 233 | 233 |
| 217 | 221 | 223 | 225 | 227 | 229 | 229 | 231 | 233 | 235 |

LIGHT SOURCE MODULE

CROSS REFERENCE TO RELATED APPLICATION

This application claims the benefits of the Taiwan Patent Application Serial Number 105116261, filed on May 25, 2016, the subject matter of which is incorporated herein by reference.

BACKGROUND OF THE INVENTION

1. Field of the Invention

The present invention relates to a light source module, particularly, to a light source module simulating the spectrum of sunlight underwater.

2. Description of Related Art

In nature, sunlight serves as the main light source of the environment for the living organisms. The sunlight received at different geographical environments and latitudes may have different spectrum, therefore, the organism species vary at the different regions. However, the natural light received by the organisms in the artificial nurturing environment differs from that in the natural environment. Accordingly, the organisms grew by artificial cultivation usually fail to achieve their best growth condition due to the light source.

In order to improve the growth efficiency of the organisms, the artificial light source may be utilized for artificial cultivation to fulfill the need of illumination. The conventional artificial light sources for the plant cultivation mainly include incandescent lamp, daylight lamp, halogen lamp, high-pressure sodium lamp, fluorescent lamp, or the like, however, the spectrum of the lights emitted by those artificial light sources do not match with the spectrums of natural lights of their natural living environments, and even some of the artificial light sources may generate heat radiation which causes overheated plants. Therefore, those artificial light sources cannot serve as ideal light sources to improve the growing rate of plants. Although the artificial light source simulating sunlight has been developed, the sunlight spectrum underwater differs from the sunlight spectrum on the ground. Therefore, the current light source simulating the sunlight cannot provide the light source with the best light condition that needed by aquatic organisms.

Therefore, it is desirable to develop an artificial light source that simulates the sunlight underwater with low heat radiation in order to provide the illumination needed for the aquatic organisms.

SUMMARY OF THE INVENTION

The object of the present invention is to provide a light source module, which may simulate the spectrum of sunlight underwater with low heat radiation. The light source module of the present invention may be utilized to cultivate aquatic organisms for increasing the growing rate of those aquatic organisms.

To achieve the object, the present invention provides a light source module, which comprises: a wiring board; and a light emitting diode (LED) array electrically connected to the wiring board. The LED array may be driven to emit a first group of emission peaks, a second group of emission peaks, and a third group of emission peaks, wherein the first group of emission peaks includes a plurality of emission peaks in a range of 300 nm≤$\kappa_{max}$<450 nm, the second group of emission peaks includes a plurality of emission peaks in a range of 450 nm≤$\lambda_{max}$<550 nm, and a third group of emission peaks includes a plurality of emission peaks in a range of 550 nm≤$\lambda_{max}$<600 nm. Those emission peaks match the spectrum of sunlight underwater. A peak intensity $I_a$ of each emission peak in the first group is in a range of 0<$I_a$≤0.9 and a peak intensity $I_b$ of each emission peak in the third group is in a range of 0<$I_b$≤0.9 when a maximum peak intensity of the emission peaks in the second group is taken as 1.0. Herein, the maximum peak intensity of the first group of emission peaks is preferably 0.5 to 0.9, and most preferably 0.6 to 0.9; the maximum peak intensity of the third group of emission peaks is preferably 0.1 to 0.8, and most preferably 0.1 to 0.7. In addition, a fourth group of emission peaks is further emitted when the LED array is driven, wherein the fourth group of emission peaks includes at least one emission peak in a range of 600 nm≤$\lambda_{max}$<700 nm. A peak intensity $I_c$ of each emission peak in a range of 0<$I_c$≤0.5 when the maximum peak intensity of the emission peaks in the second group is taken as 1.0.

Accordingly, the light emitting units with different wavelengths in the LED array may be mixed and combined to provide the light needed for the aquatic organisms. Since the light source provided by the light source module is luminescence, the problems of rising temperature of the environment of those aquatic organisms due to the artificial light may be prevented. For example, when the light source module is utilized as a grow light for cultivating the water aquatic plants, the problems of overheated plants caused by the heat radiation may be prevented, thus the cost for lowering the temperature may be decreased and the close illumination may be achieved. In addition, the LED array of the present invention may be driven in various ways through the circuit design, accordingly, the light emitting units of the LED array may be driven to match the spectrum of the sunlight, and alternatively, specific light emitting units of the LED array may be driven to give the desired light module such as blue light mode to make the coral fluorescent more apparent, or reinforce the red light to make the red coral more significant.

In the present invention, the LED array may be arranged in a N×M array (N and M are positive integer, N≥3, M≥2) and light emitting units with different wavelength preferably be arranged in the mosaic mode to evenly mix the light. For example, the four adjacent light emitting units preferably provide at least two emission peaks with different peak wavelength ($\lambda_{max}$) to form a partial 2×2 sub-array of mixed light, thus the light mixing effect of the LED array may be improved based on a plurality of the partial sub-array of mixed light. However, the arrangement of the LED array is not limited to the aforementioned mosaic mode and the LED array can be arranged in the straight mode (that is, the light emitting units having the same wavelength may be arranged adjacently in longitudinal or transverse direction) or other arrangements.

In the present invention, each light emitting unit includes a LED chip, the emission peaks may be provided directly by a plurality of LED chips having different wavelengths. Alternatively, the LED chips may be used as the excitation source to excite the fluorescence material layer covered on the LED chips to emit light as a portion of the light emitting unit. For example, UV light or blue light with $\lambda_{max}$ of 200-490 nm may be used as the excitation source to excite the fluorescence material layer to emit the light with emission peaks ranging in 510 nm≤$\lambda_{max}$<600 nm and with a CIE1931 color coordinate of 0.1≤x≤0.65 and 0.35≤y≤0.85. Accordingly, compare to green light LED chip, the green light emitted from the fluorescence material layer excited by the UV or blue light LED chip may give better luminous efficiency. Herein, the light emitted from the fluorescence with emission peaks ranging in 510 nm≤$\lambda_{max}$<600 nm may further has the waveband in the range of 620 nm to 780 nm to simulate the spectrum of sunlight underwater having red light wave band. Similarly, the light with emission peaks ranging in 600 nm≤$\lambda_{max}$<700 may be provided directly from the red light LED chip or light emitted from the red fluorescence material layer which is excited by UV or blue light LED chip. Here, the excitation light emitted from the LED excitation source may completely be absorbed by the fluorescence material layer comprising single or numerous fluorescent powders so that the light emitted by each of the light emitting unit has the emission peak of the fluorescent material layer, or may partially be absorbed by the fluorescence material layer so that portion of the excitation light penetrates through the fluorescence material layer will mix with the fluorescence light emitted from the fluorescence material layer to give white light or other colored light. Furthermore, the fluorescence material layer is not particularly limited, suitable fluorescence material may be chosen according to practical needs. For example, fluorescence materials having emission peaks with color coordinate (CIE1931) of 0.1≤x≤0.75 and 0.15≤y≤0.85 are suitable for the present invention, but the present invention is not limited thereto.

In the present invention, the wavelength difference ($\Delta\lambda_{max}$) between two adjacent peak values of those emission peaks is not particularly limited, and can be separated with a fixed or unfixed wavelength difference ($\Delta\lambda_{max}$) according to practical needs. For example, one embodiment of the present invention matches the LED/fluorescence light with 20 nm wavelength difference to simulate the spectrum of sunlight, but the present invention is not limited thereto.

In the present invention, the wiring board is not particular limited, and can be a single plate, a double plate, a triple plate, or other plates that provide the LED array to electrically connect thereon. In addition, the LED packaging method of the present invention is not particularly limited, for example, the LED chips are preferably packaged to form the surface mount LED elements for the following steps of mounting the surface mount elements with different wavelength on the wiring board.

In addition, the present invention further provides a use of the aforementioned light source module, which can be used to provide the light source for cultivating aquatic organisms and increase the growing rate of the aquatic organisms.

BRIEF DESCRIPTION OF THE DRAWINGS

FIG. 14 is a schematic view of the LED array arranged in the mosaic mode of the second embodiment of the present invention.

FIG. 16 is a schematic view of the LED array arranged in the straight mode of the second embodiment of the present invention.

FIG. 22 is a schematic view of the LED array arranged in the straight mode of another aspect of the second embodiment of the present invention.

FIG. 26 is a schematic view of the LED array arranged in the straight mode of another aspect of the second embodiment of the present invention.

FIG. 30 is a schematic view of the LED array arranged in the straight mode of another aspect of the second embodiment of the present invention.

FIG. 34 is a schematic view of the LED array arranged in the straight mode of another aspect of the second embodiment of the present invention.

FIG. 38 is a schematic view of the LED array arranged in the straight mode of another aspect of the second embodiment of the present invention.

FIG. 42 is a schematic view of the LED array arranged in the straight mode of another aspect of the second embodiment of the present invention.

FIG. 46 is a schematic view of the LED array arranged in the straight mode of the third embodiment of the present invention.

DETAILED DESCRIPTION OF THE PREFERRED EMBODIMENT

Hereafter, examples will be provided to illustrate the embodiments of the present invention. Advantages and effects of the invention will become more apparent from the disclosure of the present invention. It should be noted that these accompanying figures are simplified and illustrative. The quantity, shape and size of components shown in the figures may be modified according to practical conditions, and the arrangement of components may be more complex. Other various aspects also may be practiced or applied in the invention, and various modifications and variations can be made without departing from the spirit of the invention based on various concepts and applications.

Embodiment 1

Figure 1:
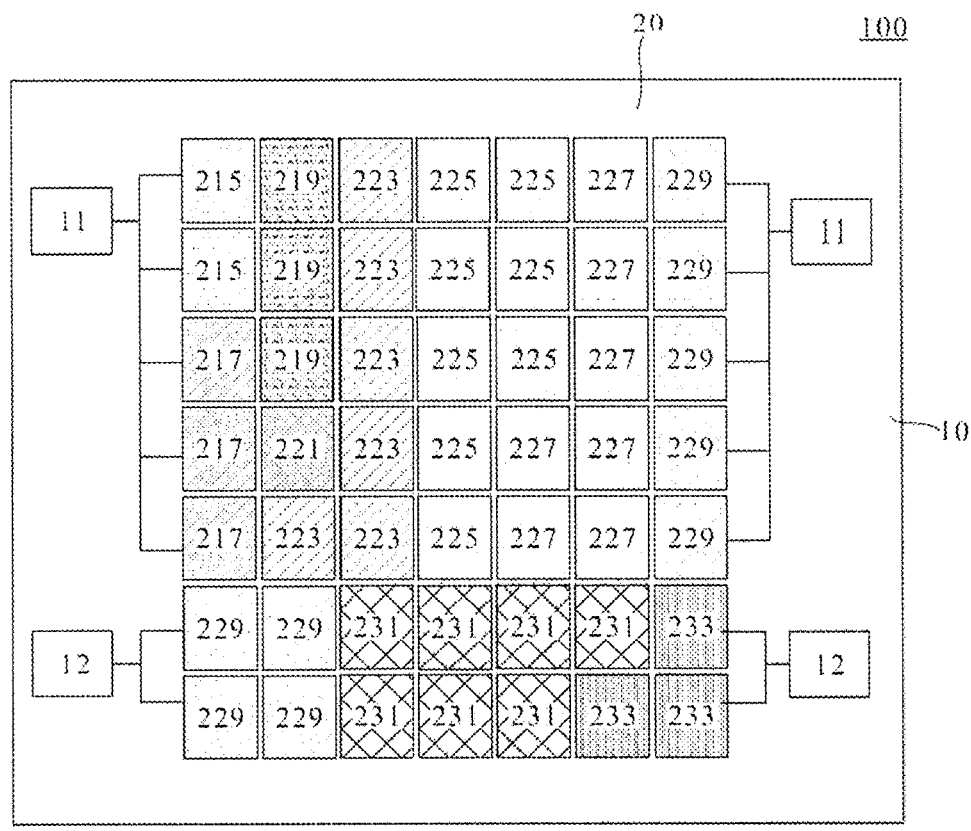
FIG. 1 is a schematic view of the light source of the first embodiment of the present invention.

Please refer to FIG. 1, which illustrates the light source module 100 of one embodiment of the present invention. As illustrated in FIG. 1, the light source module 100 of the present invention comprises a wiring board 10 and a LED array 20, wherein the LED array is configured with multi-wavelength LED elements and electrically connects to the electrodes 11, 12 of the wiring board 10. Accordingly, those multi-wavelength LED elements are utilized to simulate the spectrum of sunlight underwater. The following description exemplifies the simulation of the spectrum of sunlight 5, 10, 15, and 20 meters underwater.

First, the simulation of the spectrum of sunlight 5 meters underwater is exemplified. As illustrated in FIG. 1, two 390 nm LED elements 215, three 410 nm LED elements 217, three 430 nm LED elements 219, one 450 nm LED element 221, six 470 nm LED elements 223, eight 490 nm LED elements 225, seven 510 nm LED elements 227, nine 530 nm LED elements 229, seven 550 nm LED elements 231, and three 570 nm LED elements 233 were applied in the present invention. These 49 LED elements were used for mixing the spectrum, wherein the maximum operational voltage/current/power each of the LED elements were 3.4 V/700 mA/2.38 W.

Figure 2:
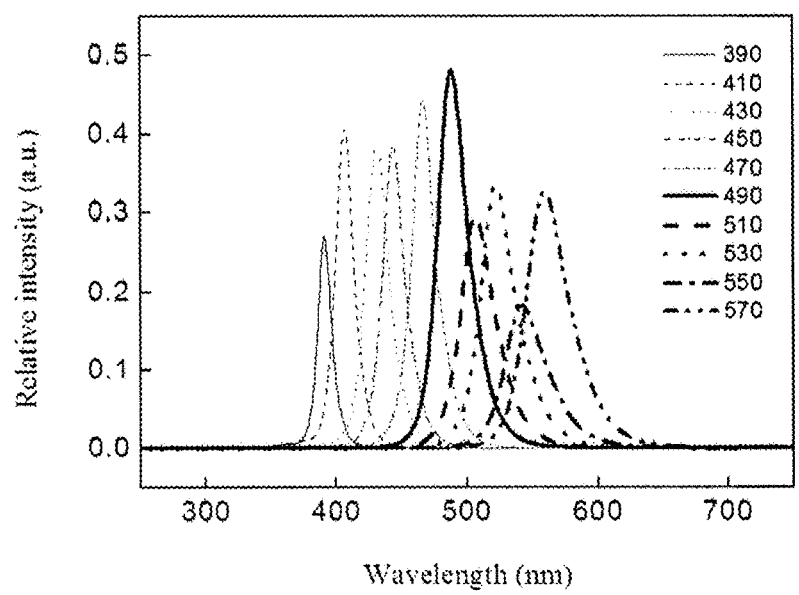
FIG. 2 shows the emission peaks emitted by the LED array that illustrated in FIG. 1.
Figure 3:
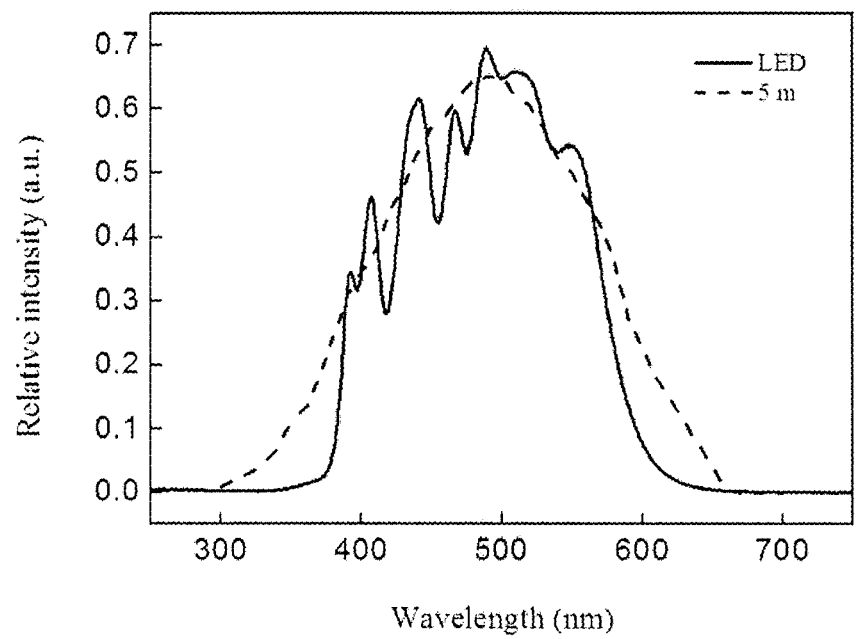
FIG. 3 shows the spectrum of the simulation light emitted by the LED array illustrated in FIG. 1 and the spectrum of the sunlight 5 meters underwater.

As illustrated in FIG. 1, those LED elements were arranged to form a 7×7 LED array 20 and were configured to 7 serial 5 parallel connecting group and 7 serial 2 parallel connecting group, wherein the 7 serial 5 parallel connecting group comprised 390 nm to 530 nm LED elements and was electrically connected to the electrode 11; the 7 serial 2 parallel connecting group comprised 530 nm to 570 nm LED elements and was electrically connected to the electrode 12. Thereby, after the LED array, 20 was driven, the emission peaks (the maximum peak intensity of the emission peaks in the first and third emission groups were 0.83 and 0.67 respectively) shown in the following table 1 and FIG. 2 may be emitted by those LED elements for mixing the simulating spectrum shown in FIG. 3.

TABLE 1

| simulation of 5 meters underwater | | |
|---|---|---|
| | Emission peak ($\lambda_{max}$) | Peak intensity ratio |
| First group of emission peaks (300 nm ≤ $\lambda_{max}$ < 450 nm) | 390 nm | 0.56 |
| | 410 nm | 0.83 |
| | 430 nm | 0.80 |
| Second group of emission peaks (450 nm ≤ $\lambda_{max}$ < 550 nm) | 450 nm | 0.79 |
| | 470 nm | 0.91 |
| | 490 nm | 1.00 |
| | 510 nm | 0.62 |
| | 530 nm | 0.68 |
| Third group of emission peaks (550 nm ≤ $\lambda_{max}$ < 600 nm) | 550 nm | 0.38 |
| | 570 nm | 0.67 |

In the present invention, the LED array 20 is not limited to the straight mode arrangement illustrated in FIG. 1, the LED array can be arranged in the mosaic mode to effectively and uniformly mix the light with multi-wavelength, or these LED elements may be configured with individual circuits so that the LED elements with different wavelength may be driven independently while the intensity of the light with different wavelength may be adjusted by voltage. Accordingly, the LED array 20 is capable of emitting the light with spectrum simulating the living environment of aquatic organisms (such as coral, algae, fish, and etc.). Also, the LED array 20 may be adjusted to a variety of light source modes (such as blue light viewing mode) based on the needs or occasion. In addition, the light source modes may be automatically switched according to the brightness or switching time set tip by the users.

Figure 4:
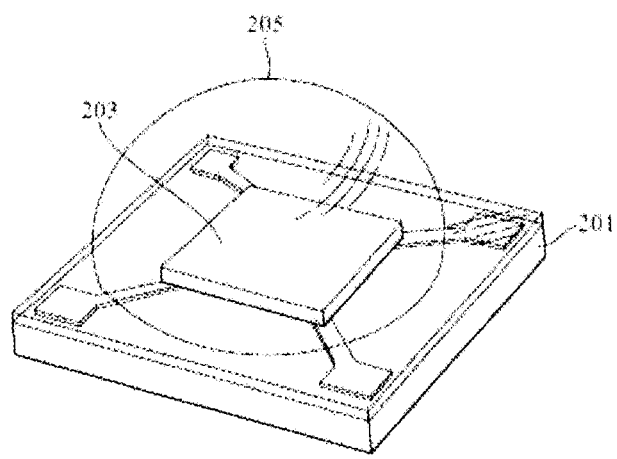
FIG. 4 is a perspective diagram of the LED elements of the first embodiment of the present invention.

In addition, the LED packaging method of the light source module 100 is not particularly limited, and the object of the present invention can be realized regardless of the packaging method. For example, the LED chips may be packaged by chip on board method which directly disposes the LED chips with aforementioned wavelength on the wiring board 10; or, the LED chips may be packaged to form the surface mount element with identical dimensions before mounting those surface mount element on the wiring board 10. Herein, the present embodiment is exemplified by using the surface mount element method. As illustrated in FIG. 4, the LED element comprises a package base 201, a LED chip 203, and a sealant layer 205, wherein the LED chip 203 was connected to the package base 201 and the LED chip 203 was covered by the sealant layer 205 to accomplish the surface mount LED element. The present embodiment directly mixed the light with multi-wavelength emitted by numerous LED chips, therefore, the sealant layer 205 used herein was transparent silicone layer without fluorescence material.

Afterward, the present embodiment utilized the same 7×7 LED array to simulate the spectrum of sunlight 10, 15, and 20 meters underwater by adjusting the number of the LED element with different wavelengths.

Figures 5, 6:
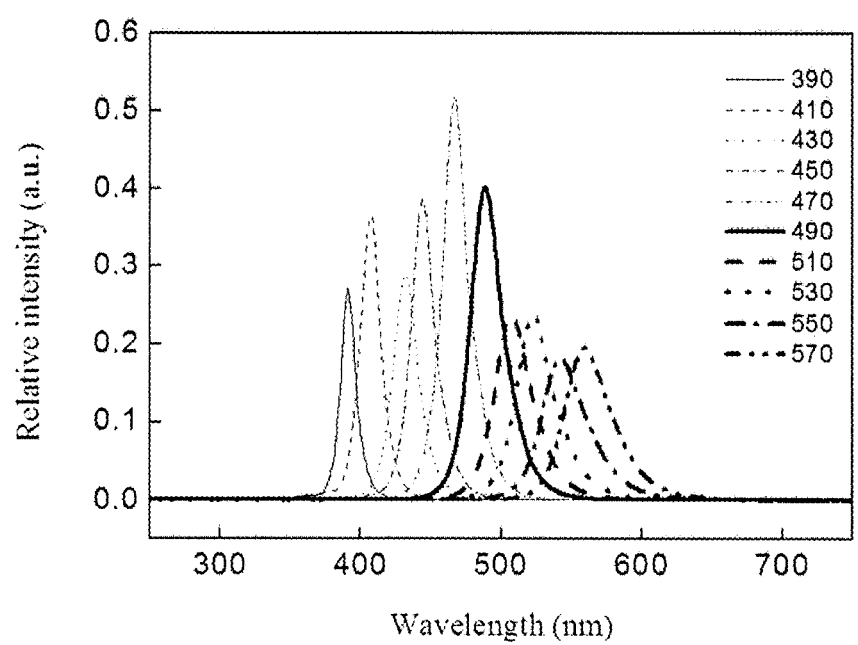
FIG. 5 is a schematic view of the LED array of another aspect of the first embodiment of the present invention.
FIG. 6 shows the emission peaks emitted by the LED array that illustrated in FIG. 5.

Please refer to FIG. 5 illustrating the embodiment of simulating the spectrum of sunlight 10 meters underwater, wherein one 390 nm LED element 215, two 410 nm LED elements 217, two 430 nm LED elements 219, three 450 nm LED elements 221, four 470 nm LED elements 223, six 490 nm LED elements 225, five 510 nm LED elements 227, six 530 nm LED elements 229, eight 550 nm LED elements 231, and twelve 570 nm LED elements 233 were applied in the present invention. The lights emitted from multi-wavelength LED chips were mixed directly. Accordingly, after the LED array of the present embodiment was driven, the emission peaks (the maximum peak intensity of the emission peaks in the first and the third emission groups were 0.70 and 0.39) shown by the following table 2 and FIG. 6 may be emitted by those LED elements for mixing the simulating spectrum shown in FIG. 7.

TABLE 2 simulation of 10 meters underwater

|  | Emission peak ($\lambda_{max}$) | Peak intensity ratio |
|---|---|---|
| First group of emission peaks (300 nm ≤ $\lambda_{max}$ < 450 nm) | 390 nm | 0.52 |
|  | 410 nm | 0.70 |
|  | 430 nm | 0.55 |
| Second group of emission peaks (450 nm ≤ $\lambda_{max}$ < 550 nm) | 450 nm | 0.74 |
|  | 470 nm | 1.00 |
|  | 490 nm | 0.78 |
|  | 510 nm | 0.47 |
|  | 530 nm | 0.46 |
| Third group of emission peaks (550 nm ≤ $\lambda_{max}$ < 600 nm) | 550 nm | 0.37 |
|  | 570 nm | 0.39 |

Figures 7, 8:
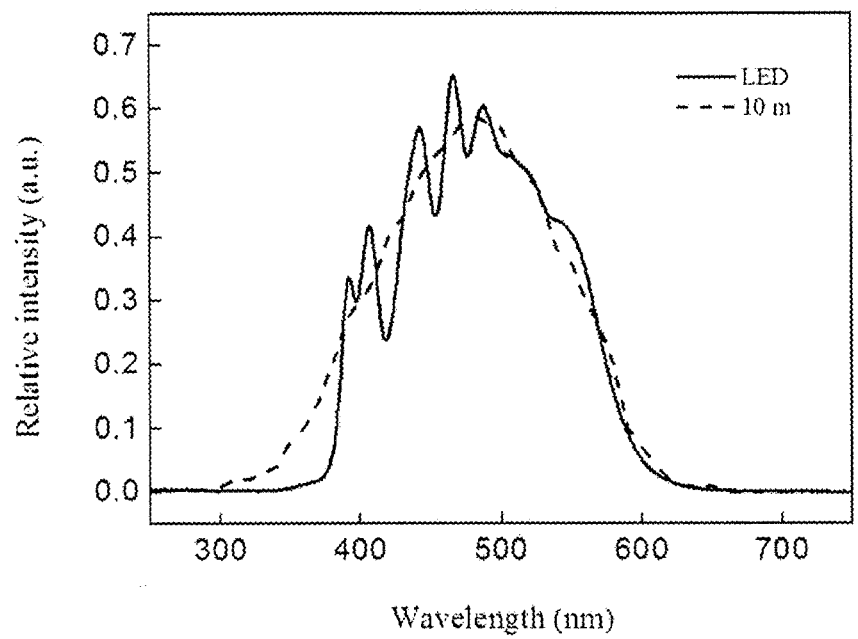
FIG. 7 shows the spectrum of the simulation light emitted by the LED array illustrated in FIG. 5 and the spectrum of the sunlight 10 meters underwater.
FIG. 8 is a schematic view of the LED array of yet another aspect of the first embodiment of the present invention.
Figure 9:
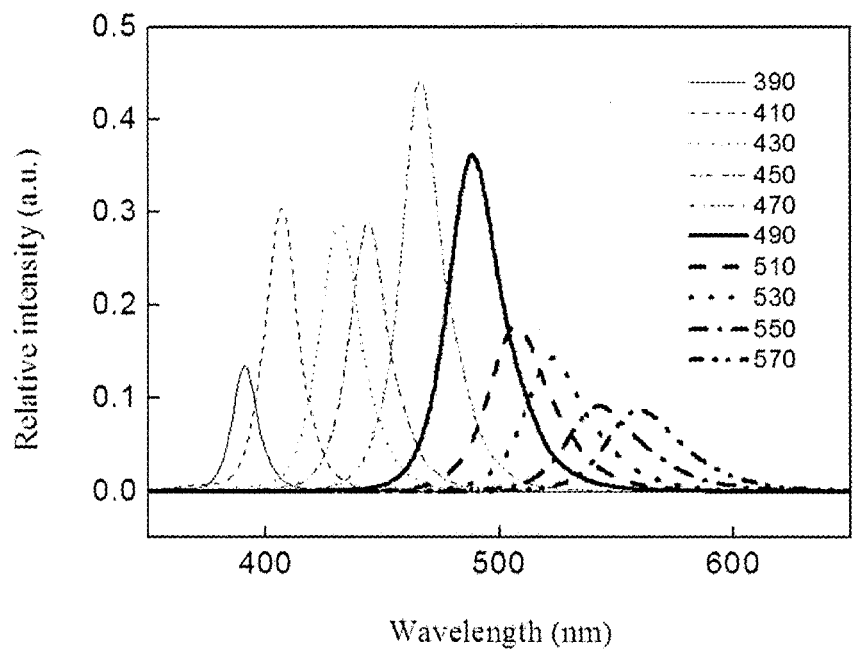
FIG. 9 shows the emission peaks emitted by the LED array that illustrated in FIG. 8.
Figure 10:
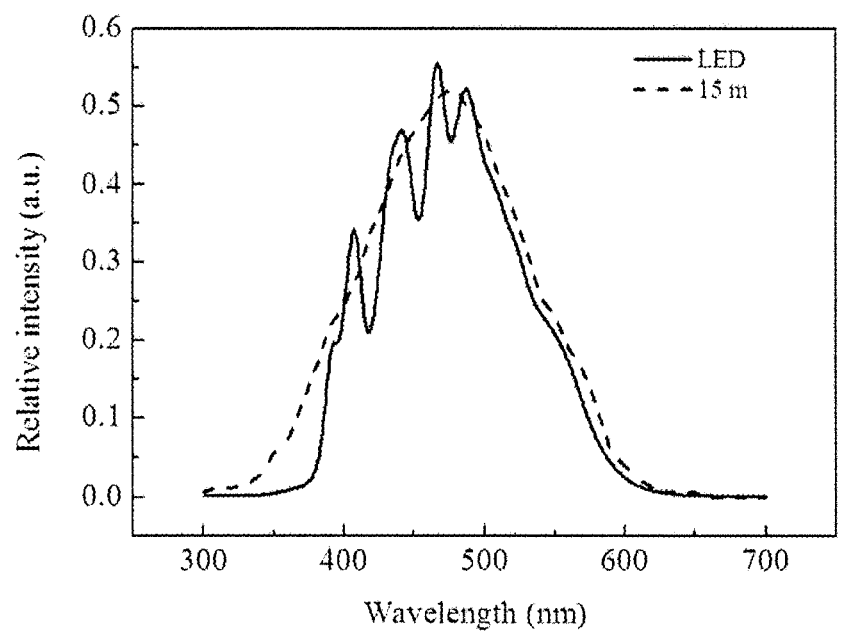
FIG. 10 shows the spectrum of the simulation light emitted by the LED array illustrated in FIG. 8 and the spectrum of the sunlight 15 meters underwater.

Please refer to FIG. 8 illustrating the embodiment of simulating the spectrum of sunlight 15 meters underwater, wherein one 390 nm LED element 215, three 410 nm LED elements 217, three 430 nm LED elements 219, three 450 nm LED elements 221, six 470 nm LED elements 223, eight 490 nm LED elements 225, six 510 nm LED elements 227, six 530 nm LED elements 229, six 550 nm LED elements 231, and seven 570 nm LED elements 233 were applied in the present invention. The lights emitted from multi-wavelength LED chips were mixed directly. Thereby, after the LED array of the present embodiment was driven, the emission peaks (the maximum peak intensity of the emission peaks in the first and the third emission groups were 0.68 and 0.21) shown in the following table 3 and FIG. 9 may be emitted by those LED elements for mixing the simulating spectrum shown in FIG. 10.

TABLE 3 simulation of 15 meters underwater

|  | Emission peak ($\lambda_{max}$) | Peak intensity ratio |
|---|---|---|
| First group of emission peaks (300 nm ≤ $\lambda_{max}$ < 450 nm) | 390 nm | 0.30 |
|  | 410 nm | 0.68 |
|  | 430 nm | 0.67 |
| Second group of emission peaks (450 nm ≤ $\lambda_{max}$ < 550 nm) | 450 nm | 0.65 |
|  | 470 nm | 1.00 |
|  | 490 nm | 0.82 |
|  | 510 nm | 0.41 |
|  | 530 nm | 0.34 |
| Third group of emission peak (550 nm ≤ $\lambda_{max}$ < 600 nm) | 550 nm | 0.21 |
|  | 570 | 0.20 |

Figures 11, 12:
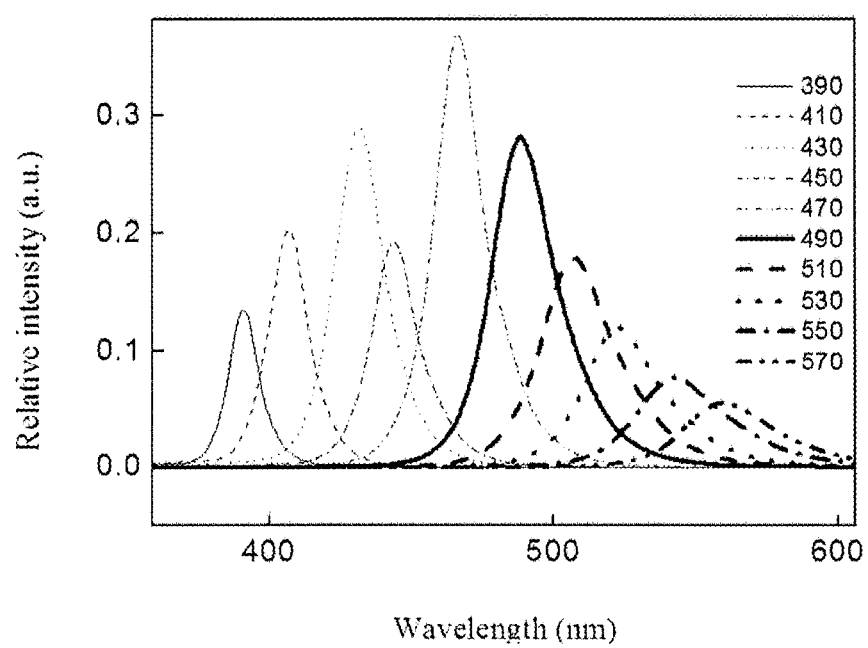
FIG. 11 is a schematic view of the LED array of another aspect of the first embodiment of the present invention.
FIG. 12 shows the emission peaks emitted by the LED array that illustrated in FIG. 11.
Figure 13:
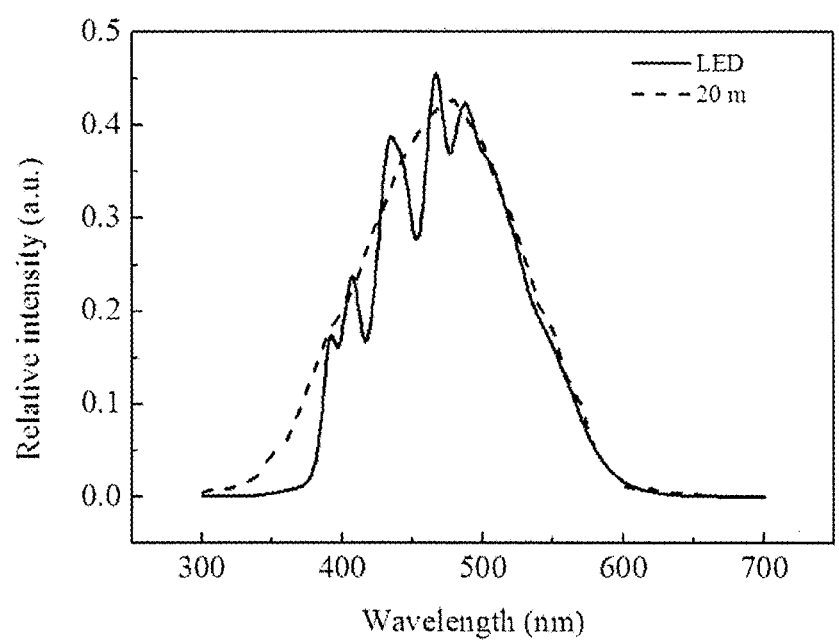
FIG. 13 shows the spectrum of the simulation light emitted by the LED array illustrated in FIG. 11 and the spectrum of the sunlight 20 meters underwater.

Please refer to FIG. 11 illustrating the embodiment of simulating the spectrum of sunlight 20 meters underwater, wherein one 390 nm LED element 215, two 410 nm LED elements 217, four 430 nm LED elements 219, two 450 nm LED elements 221, six 470 nm LED elements 223, nine 490 nm LED elements 225, seven 510 nm LED elements 227, six 530 nm LED elements 229, six 550 nm LED elements 231, and six 570 nm LED elements 233 were applied in the present invention. The lights emitted from multi-wavelength LED chips were mixed directly. Thereby, after the LED array of the present embodiment was driven, the emission peaks (the maximum peak intensity of the emission peaks in the first and the third emission groups were 0.77 and 021) shown in the following table 4 and FIG. 12 may be emitted by those LED elements for mixing the simulating spectrum shown in FIG. 13.

TABLE 4 simulation of 20 meters underwater

|  | Emission peak ($\lambda_{max}$) | Peak intensity ratio |
|---|---|---|
| First group of emission peaks (300 nm ≤ $\lambda_{max}$ < 450 nm) | 390 nm | 0.36 |
|  | 410 nm | 0.54 |
|  | 430 nm | 0.77 |
| Second group of emission peaks (450 nm ≤ $\lambda_{max}$ < 550 nm) | 450 nm | 0.52 |
|  | 470 nm | 1.00 |
|  | 490 nm | 0.75 |
|  | 510 nm | 0.48 |
|  | 530 nm | 0.33 |
| Third group of emission peaks (550 nm ≤ $\lambda_{max}$ < 600 nm) | 550 nm | 0.21 |
|  | 570 nm | 0.14 |

Embodiment 2

Please refer to FIG. 14, which illustrates the LED array 20 of another embodiment of the present invention. The present embodiment utilized 100 light emitting elements to simulate the spectrum of sunlight 5, 10, 15, and 20 meters underwater.

Figure 15:
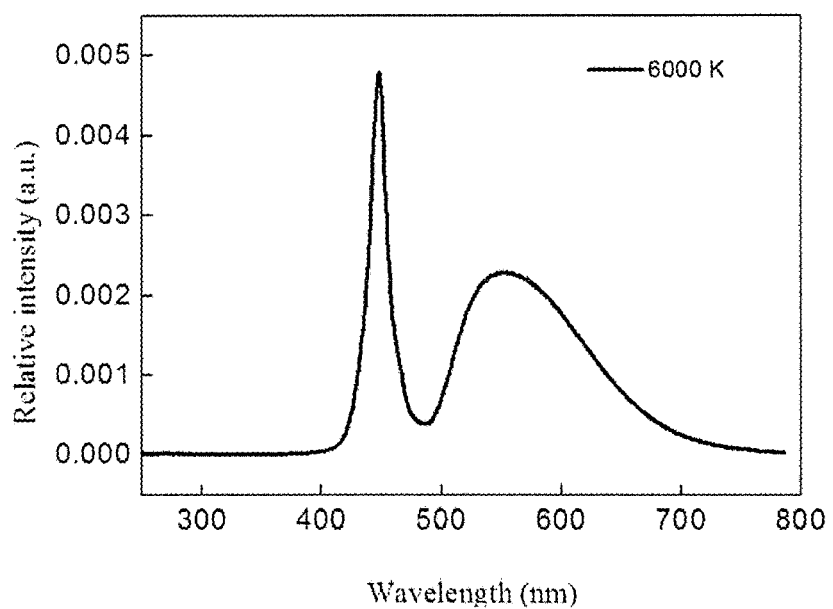
FIG. 15 shows the spectrum of the 6000K white of the second embodiment of the present invention.

First, the simulation of the spectrum of sunlight 5 meters under water is exemplified. As illustrated in FIG. 14, three 350 nm LED elements 211, three 370 nm LED elements 213, two 390 nm LED elements 215, three 410 nm LED elements 217, four 430 nm LED elements 219, one 450 nm LED element 221, six 470 nm LED elements 223, eleven 490 nm LED elements 225, six 510 nm LED elements 227, twelve 530 nm LED elements 229, eight 550 nm LED elements 231, eighteen 570 nm LED elements 233, ten 590 nm LED elements 235 were applied in the present embodiment, wherein the lights with multi-wavelength that emitted from the LED chips directly. 10×10 LED array 20 was accomplished matching those LED elements and thirteen white light LED elements 251. Herein, as illustrated in FIG. 15, the blue light LED chips, which emit the 400-490 nm excitation light ($\lambda_{max}$ approximately be 450 nm) served as the LED excitation light source of the white light LED element 251, and the sealant layer that covered the LED excitation light source was fluorescence material layer, which may emit the fluorescence light with peak value ($\lambda_{max}$) 550 nm approximately be 550 nm. Accordingly, 6000K white light may be generated by mixing the 400-490 nm LED excitation light and the 490-750 nm fluorescence light.

As illustrated in FIG. 14, those light emitting elements with different wavelength were preferably arranged as a 10×10 LED array 20 in mosaic mode in order to achieve the uniform mixed light. As shown in FIG. 14, any four adjacent light emitting elements in the LED array 20 may provide at least two emission peaks with different peak value to form a 2×2 array of partially mixed light. However, the arrangement in mosaic mode was one of the embodiments of the present invention; the 10×10 LED array of the present embodiment may be arranged in the straight mode as illustrated in FIG. 16, but not limited thereto.

Figure 17:
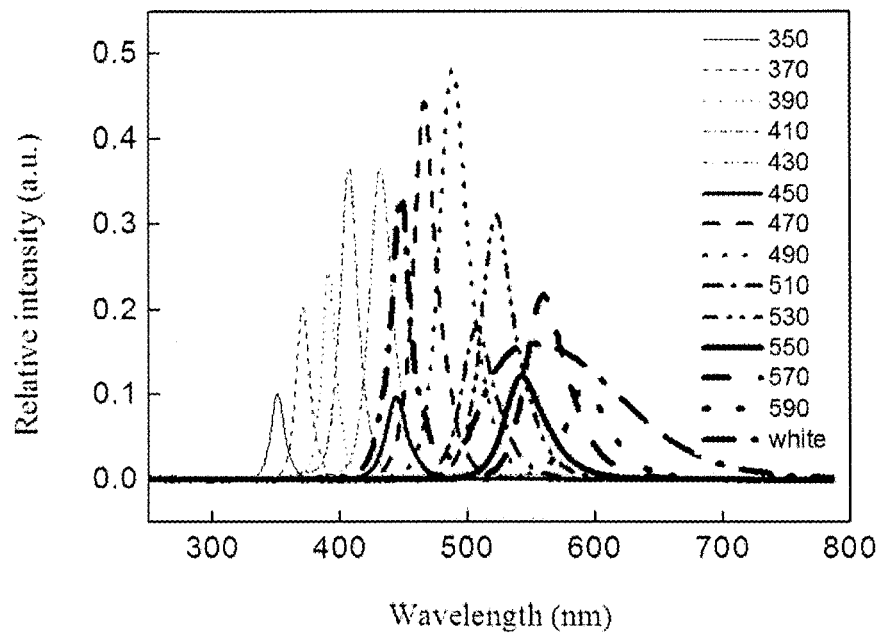
FIG. 17 shows the emission peaks emitted by the LED arrays illustrated in FIG. 14 and FIG. 16.
Figure 18:
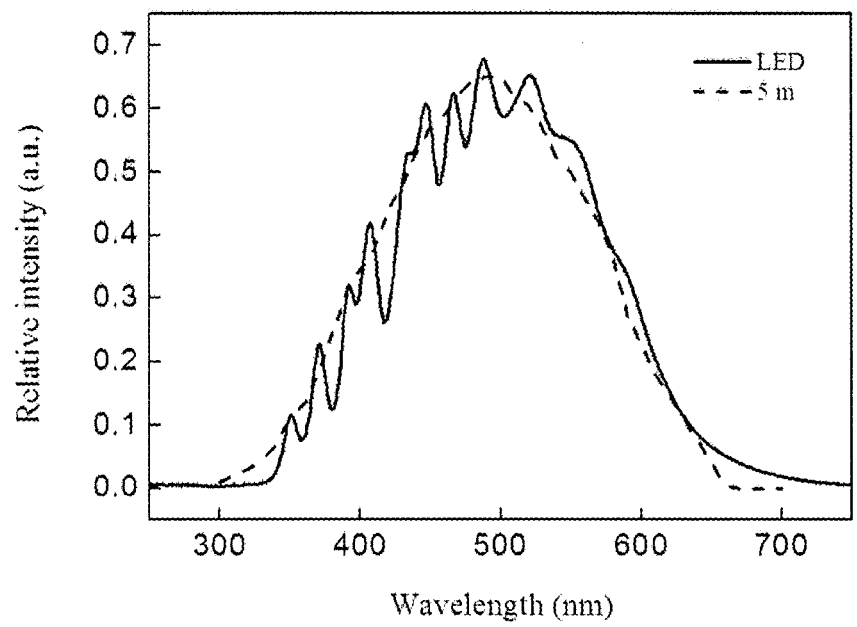
FIG. 18 shows the spectrum of the simulation lights emitted by the LED arrays illustrated in FIG. 14 and FIG. 16 and the spectrum of the sunlight 5 meters underwater.

Accordingly, after the LED array 20 was driven, the emission peaks (the maximum peak intensity of the emission peaks in the first and the third emission groups were 0.76 and 0.46) shown in the following table 5 and FIG. 17 may be emitted by those light emitting elements for mixing the simulating spectrum shown in FIG. 18.

TABLE 5 simulation of 5 meters underwater

|  | Emission peak ($\lambda_{max}$) | Peak intensity value |
|---|---|---|
| First group of emission peaks (300 nm ≤ $\lambda_{max}$ < 450 nm) | 350 nm | 0.21 |
|  | 370 nm | 0.42 |
|  | 390 nm | 0.49 |
|  | 410 nm | 0.76 |
|  | 430 nm | 0.75 |
| Second group of emission peaks (450 nm ≤ $\lambda_{max}$ < 550 nm) | 450 nm | 0.20 |
|  | 450 nm (Excitation light of white light LED element) | 0.71 |
|  | 470 nm | 0.92 |
|  | 490 nm | 1.00 |
|  | 510 nm | 0.37 |
|  | 530 nm | 0.64 |
| Third group of emission peaks (550 nm ≤ $\lambda_{max}$ < 600 nm) | 550 nm | 0.25 |
|  | 550 nm (Fluorescence light of white light LED element) | 0.34 |
|  | 570 nm | 0.46 |
|  | 590 nm | 0.24 |

Figure 19:
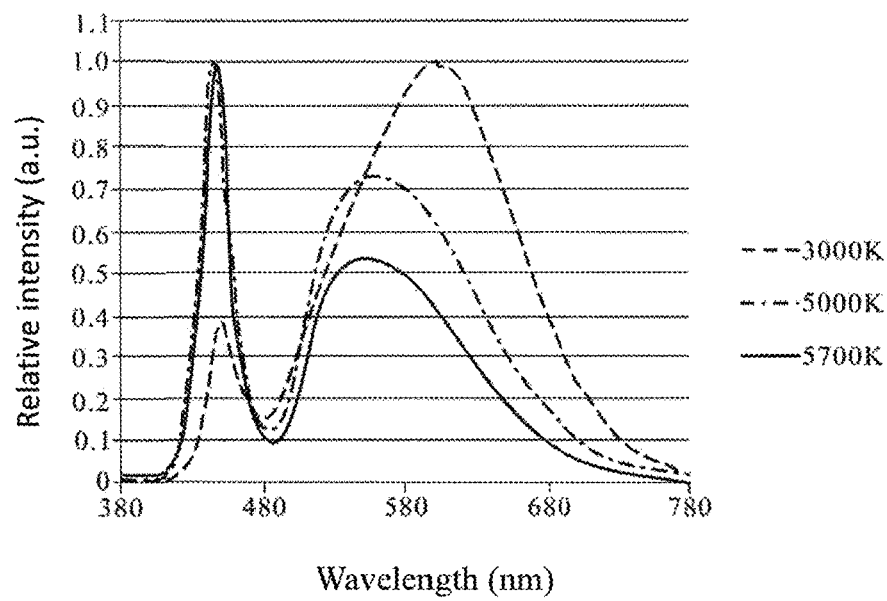
FIG. 19 shows the spectrum of the 3000K, 5000K, and 5700K white light of the second embodiment of the present invention.
Figure 20:
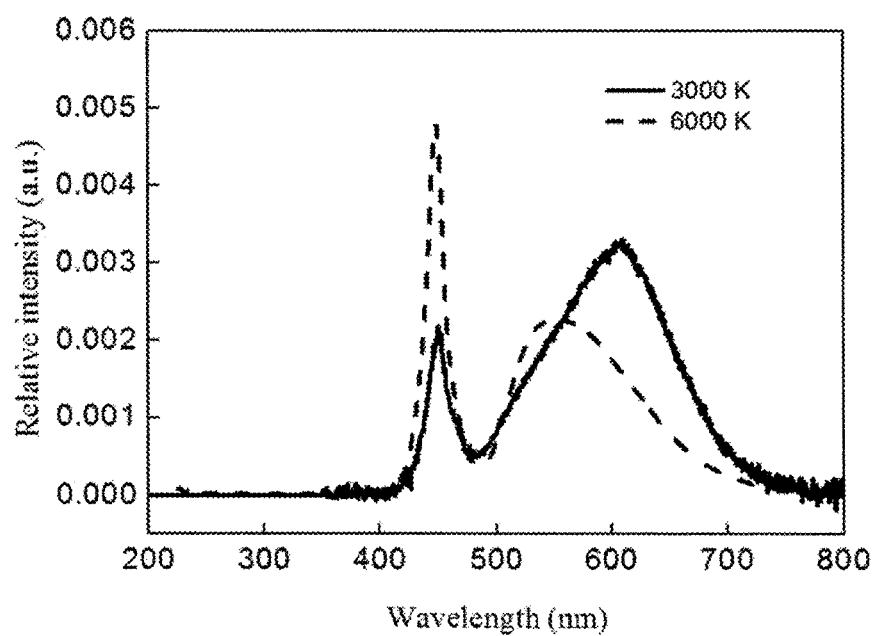
FIG. 20 shows the spectrum of the 3000K and 6000K white light of the second embodiment of the present invention.

It should be particularly noted that in the embodiment of matching the LED chip and fluorescence material, the relative intensity of the LED excitation light and the fluorescence light may be adjusted by altering the thickness of the fluorescence material layer or the concentration of the fluorescence material. For example, despite that the fluorescence material layer adsorbed partial of the excitation light in the aforementioned embodiment, the fluorescence material layer may be adjusted so that the excitation light emitted by the LED may be absorbed completely by the fluorescence material layer. In addition, the white light used in the present embodiment is not particularly limited to 6000K white light and other fluorescence material layer may be used. For example, 3000K, 5000K, or 57000K white light may be used (the spectrum thereof are shown in FIG. 19 and FIG. 20) but not limited thereto. Moreover, due to the poor luminous efficiency of the LED chip with a longer wavelength, the emission peak with longer wavelength may be provided by exciting the fluorescence material layer using LED light to improve the luminous efficiency. For example, the excitation light may be provided by blue light or UV light LED chip with $\lambda_{max}$ ranging in 200 nm to 490 nm to excite the fluorescence material layer to emit the light with emission peak (yellow-green light) ranging in 510 nm≤$\lambda_{max}$<600 nm or light with emission peak (red light) ranging in 600 nm≤$\lambda_{max}$<700 nm.

Next, the present embodiment utilized the same 10×10 LED array and adjusted the numbers of each LED elements with a different wavelength to simulate the spectrum of sunlight 10, 15, and 20 meters underwater.

Figure 21:
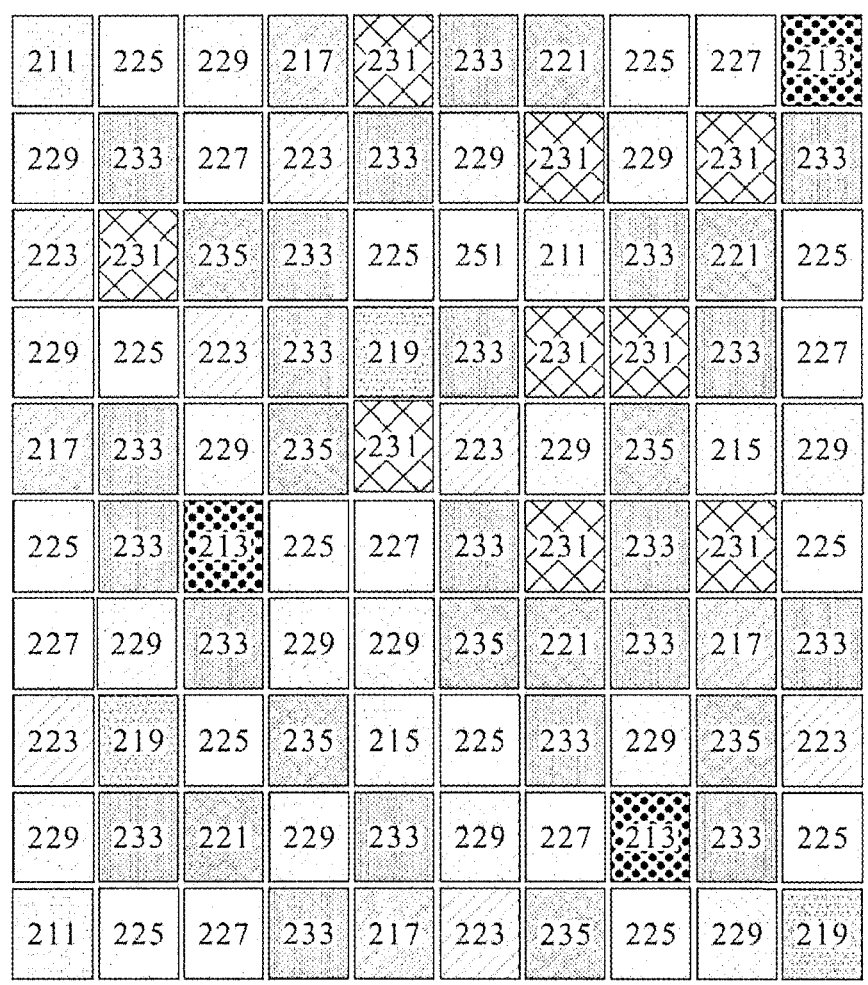
FIG. 21 is a schematic view of the LED array arranged in the mosaic mode of another aspect of the second embodiment of the present invention.
Figure 23:
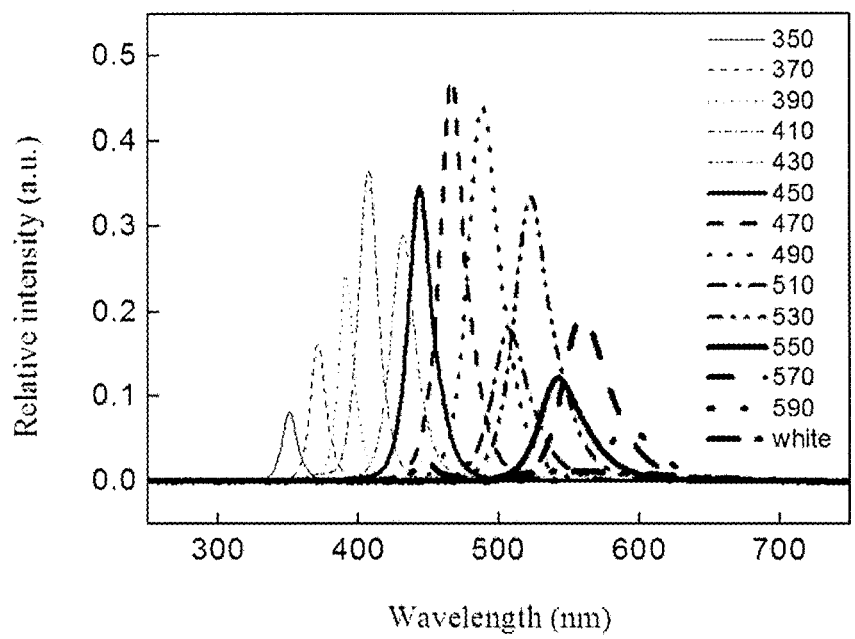
FIG. 23 shows the emission peaks emitted by the LED arrays illustrated in FIG. 21 and FIG. 22.
Figure 24:
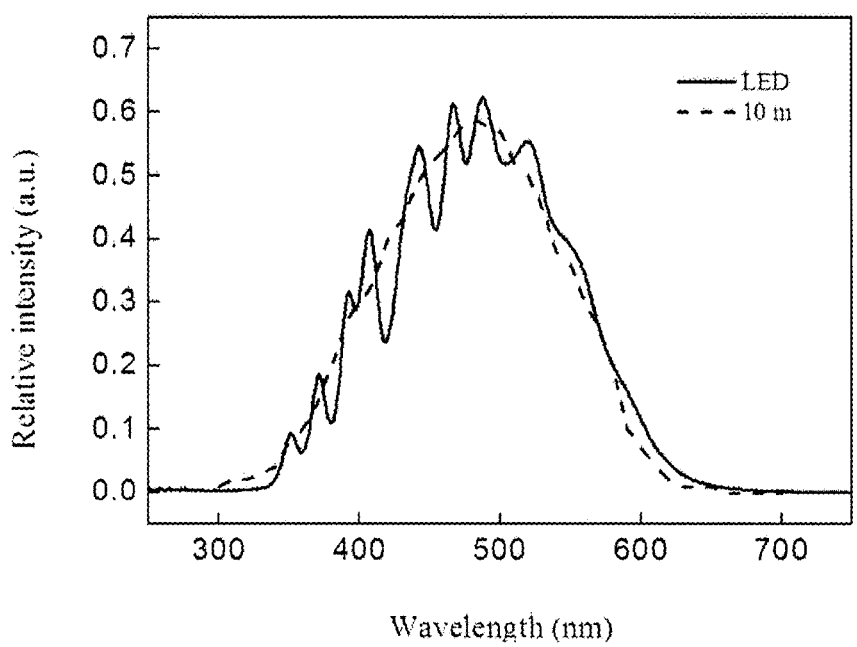
FIG. 24 shows the spectrums of the simulation lights emitted by the LED arrays illustrated in FIG. 21 and FIG. 22 and the sunlight 10 meters underwater.

First, the simulation of the spectrum of sunlight 10 meters underwater is exemplified. As illustrated in FIG. 21, three 350 nm LED elements 211, three 370 nm LED elements 213, two 390 nm LED elements 215, four 410 nm LED elements 217, three 430 nm LED elements 219, four 450 nm LED elements 221, seven 470 nm LED elements 223, thirteen 490 nm LED elements 225, seven 510 nm LED elements 227, sixteen 530 nm LED elements 229, nine 550 nm LED elements 231, twenty-one 570 nm LED elements 233, seven 590 nm LED elements 235 were applied in the present embodiment, wherein the lights with multi-wavelength emitted from the LED chips directly. Simultaneously, one white light LED element 251 was used, in which the excitation light provided by LED excitation source may mix with the fluorescence light emitted from the excited fluorescence material layer to generate white light. Similarly, the present embodiment is not limited to the mosaic mode arrangement, and may be arranged in the straight mode as illustrated in FIG. 22, but not limited thereto. Accordingly, after the LED array of the present embodiment was driven, the emission peaks (the maximum peak intensity of the emission peaks in the first and the third emission groups were 0.79 and 0.43) shown in the following table 6 and FIG. 23 may be emitted by those light emitting elements for mixing the simulating spectrum shown in FIG. 24.

TABLE 6 simulation of 10 meters underwater

|  | Emission peak ($\lambda_{max}$) | Peak intensity ratio |
|---|---|---|
| First group of emission peaks (300 nm ≤ $\lambda_{max}$ < 450 nm) | 350 nm | 0.17 |
|  | 370 nm | 0.34 |
|  | 390 nm | 0.52 |
|  | 410 nm | 0.79 |
|  | 430 nm | 0.62 |
| Second group of emission peaks (450 nm ≤ $\lambda_{max}$ < 550 nm) | 450 nm | 0.74 |
|  | 450 nm (Excitation light of white light LED element) | 0.07 |
|  | 470 nm | 1.00 |
|  | 490 nm | 0.94 |
|  | 510 nm | 0.38 |
|  | 530 nm | 0.72 |

TABLE 6-continued simulation of 10 meters underwater

| | Emission peak ($\lambda_{max}$) | Peak intensity ratio |
|---|---|---|
| Third group of emission peaks (550 nm ≤ $\lambda_{max}$ < 600 nm) | 550 nm | 0.26 |
| | 550 nm (Excitation light of white light LED element) | 0.04 |
| | 570 nm | 0.43 |
| | 590 nm | 0.14 |

Figure 25:
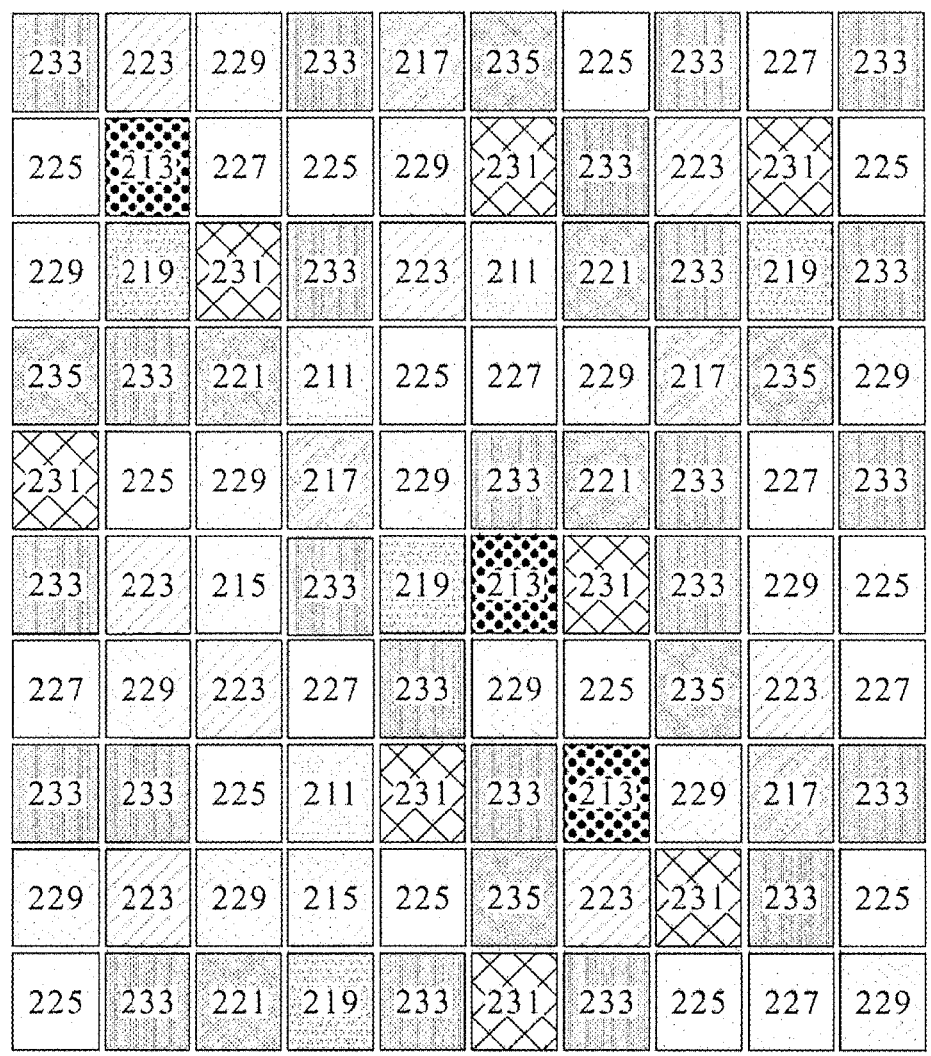
FIG. 25 is a schematic view of the LED array arranged in the mosaic mode of another aspect of the second embodiment of the present invention.
Figure 27:
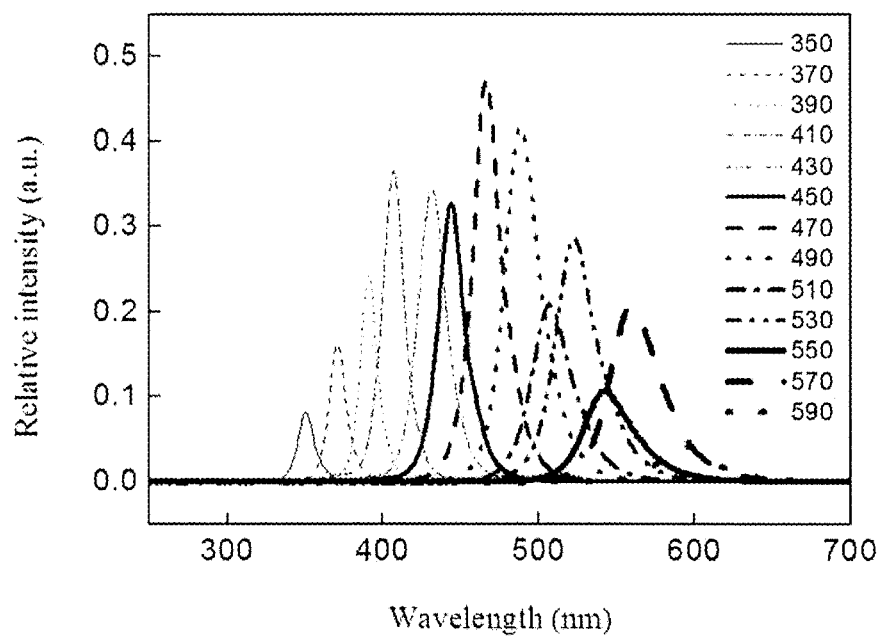
FIG. 27 shows the emission peaks emitted by the LED arrays illustrated in FIG. 25 and FIG. 26.
Figure 28:
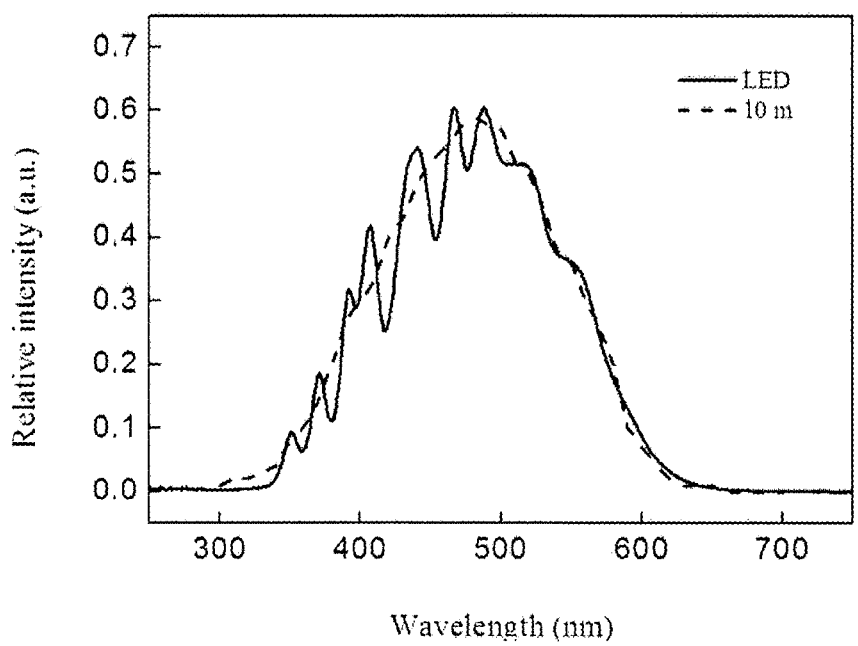
FIG. 28 shows the spectrums of the simulating lights emitted by the LED arrays illustrated in FIG. 25 and FIG. 26 and the sunlight 10 meters under water.

In addition, please refer to FIG. 25, if the white light LED element was not used for the present embodiment, the spectrum of sunlight 10 meters underwater may be simulated by using three 350 nm LED elements 211, three 370 nm LED elements 213, two 390 nm LED elements 215, four 410 nm LED elements 217, four 430 nm LED elements 219, four 450 nm LED elements 221, eight 470 nm LED elements 223, thirteen 490 nm LED elements 225, eight 510 nm LED elements 227, fourteen 530 nm LED elements 229, eight 550 nm LED elements 231, twenty-four 570 nm LED elements 233, and five 590 nm LED elements 235. Similarly, the present embodiment is not limited to the mosaic mode arrangement, and may be arranged in the straight mode as illustrated in FIG. 26, but not limited thereto. Accordingly, after the LED array of the present embodiment was driven, the emission peaks (the maximum peak intensity of the emission peaks in the first and the third emission groups were 0.76 and 0.41) shown in the following table 7 and FIG. 27 may be emitted by those light emitting elements for mixing the simulating spectrum shown in FIG. 28.

TABLE 7 simulation of 10 meters underwater

| | Emission peak ($\lambda_{max}$) | Peak intensity ratio |
|---|---|---|
| First group of emission peaks (300 nm ≤ $\lambda_{max}$ < 450 nm) | 350 nm | 0.17 |
| | 370 nm | 0.33 |
| | 390 nm | 0.50 |
| | 410 nm | 0.76 |
| | 430 nm | 0.72 |
| Second group of emission peaks (450 nm ≤ $\lambda_{max}$ < 550 nm) | 450 nm | 0.69 |
| | 470 nm | 1.00 |
| | 490 nm | 0.89 |
| | 510 nm | 0.45 |
| | 530 nm | 0.60 |
| Third group of emission peaks (550 nm ≤ $\lambda_{max}$ < 600 nm) | 550 nm | 0.23 |
| | 570 nm | 0.41 |
| | 590 nm | 0.09 |

Figure 29:
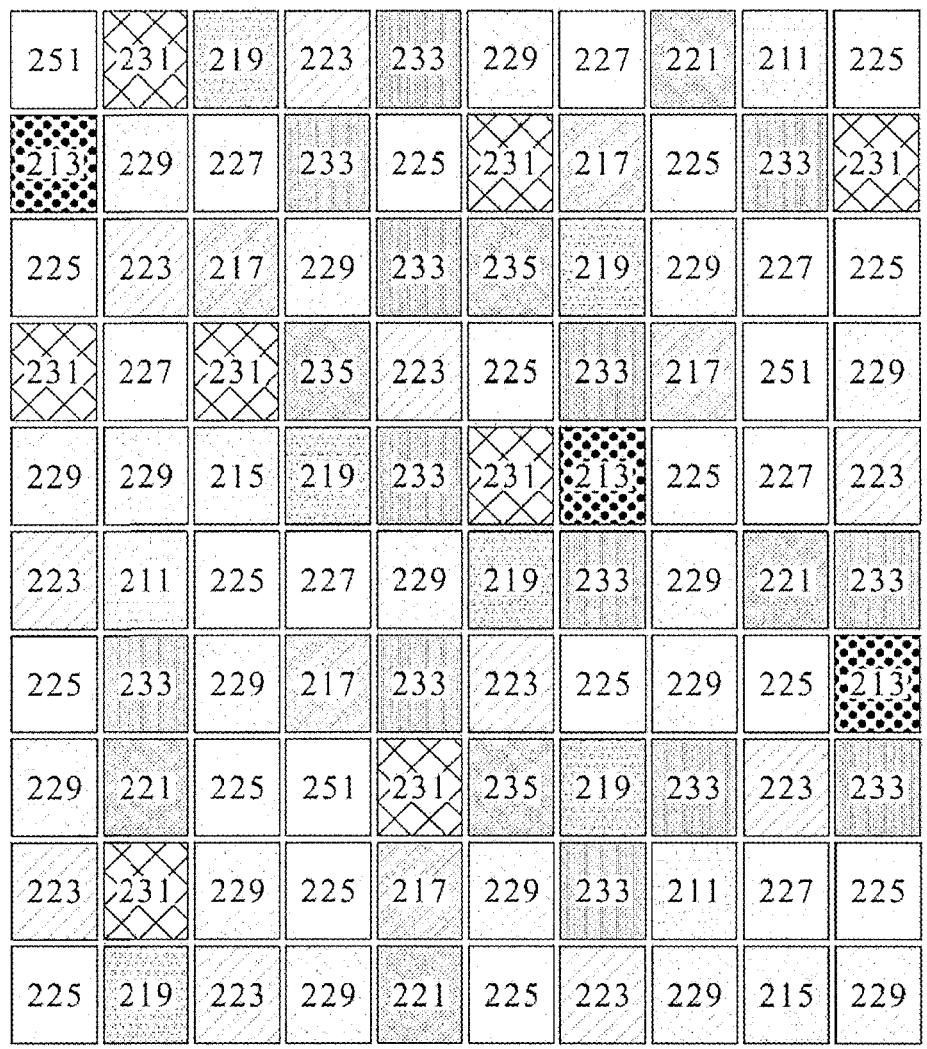
FIG. 29 is a schematic view of the LED array arranged in the mosaic mode of another aspect of the second embodiment of the present invention.
Figure 31:
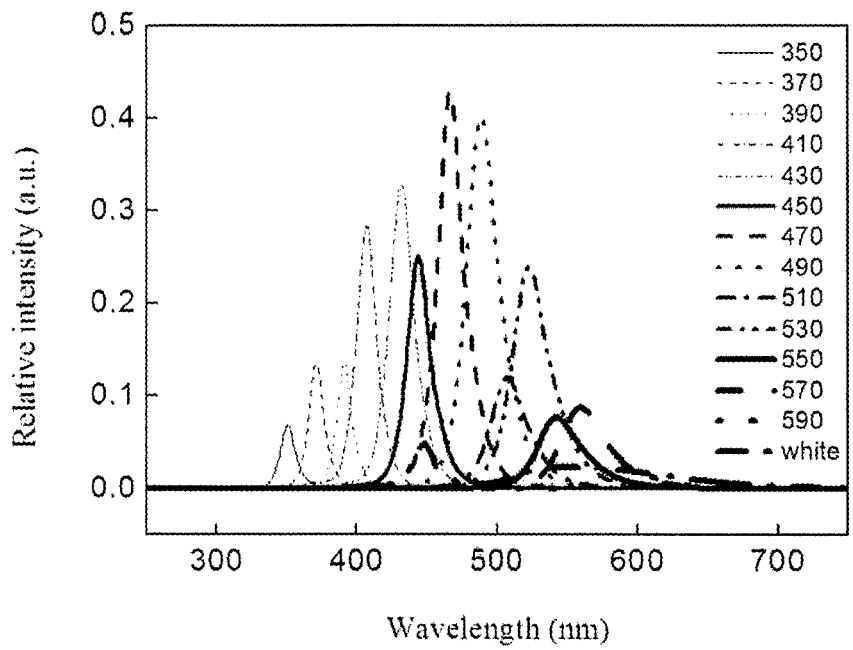
FIG. 31 shows the emission peaks emitted by the LED arrays illustrated in FIG. 29 and FIG. 30.
Figure 32:
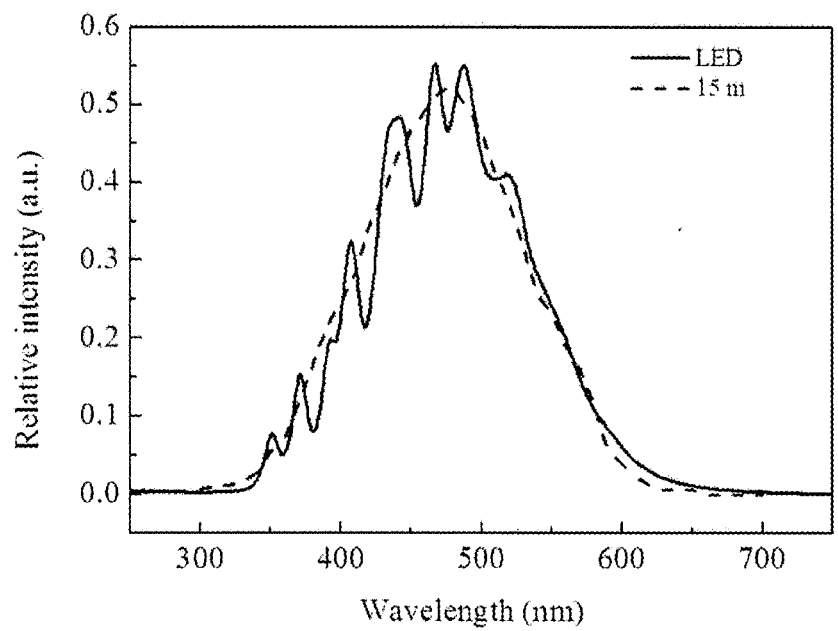
FIG. 32 shows the spectrums of the simulation lights emitted by the LED arrays illustrated in FIG. 29 and FIG. 30 and the sunlight 15 meters underwater.

The simulation of the spectrum of sunlight 15 meters underwater is exemplified. As illustrated in FIG. 29, three 350 nm LED elements 211, three 370 nm LED elements 213, two 390 nm LED elements 215, five 410 nm LED elements 217, six 430 nm LED elements 219, four 450 nm LED elements 221, ten 470 nm LED elements 223, sixteen 490 nm LED elements 225, seven 510 nm LED elements 227, seventeen 530 nm LED elements 229, eight 550 nm LED elements 231, thirteen 570 nm LED elements 233, and three 590 nm LED elements 235 were applied in the present embodiment, wherein the lights with multi-wavelength were emitted from the LED chips directly. Simultaneously, three white light LED elements 251 was used, in which the excitation light provided by LED excitation source may mix with the fluorescence light emitted from the excited fluorescence material layer to generate white light. Similarly, the present embodiment is not limited to the mosaic mode arrangement, and may be arranged in the straight mode as illustrated in FIG. 30, but not limited thereto. Accordingly, after the LED array of the present embodiment was driven, the emission peaks (the maximum peak intensity of the emission peaks in the first and the third emission groups were 0.77 and 0.22) shown in the following table 8 and FIG. 31e may be emitted by those light emitting elements for mixing the simulating spectrum shown in FIG. 32.

TABLE 8 simulation of 15 meters underwater

| | Emission peak ($\lambda_{max}$) | Peak intensity ratio |
|---|---|---|
| First group of emission peaks (300 nm ≤ $\lambda_{max}$ < 450 nm) | 350 nm | 0.16 |
| | 370 nm | 0.31 |
| | 390 nm | 0.32 |
| | 410 nm | 0.67 |
| | 430 nm | 0.77 |
| Second group of emission peaks (450 nm ≤ $\lambda_{max}$ < 550 nm) | 450 nm | 0.60 |
| | 450 nm (Excitation light of white light LED element) | 0.12 |
| | 470 nm | 1.00 |
| | 490 nm | 0.94 |
| | 510 nm | 0.28 |
| | 530 nm | 0.58 |
| Third group of emission peaks (550 nm ≤ $\lambda_{max}$ < 600 nm) | 550 nm | 0.19 |
| | 550 nm (Excitation light of white light LED element) | 0.05 |
| | 570 nm | 0.22 |
| | 590 nm | 0.07 |

Figure 33:
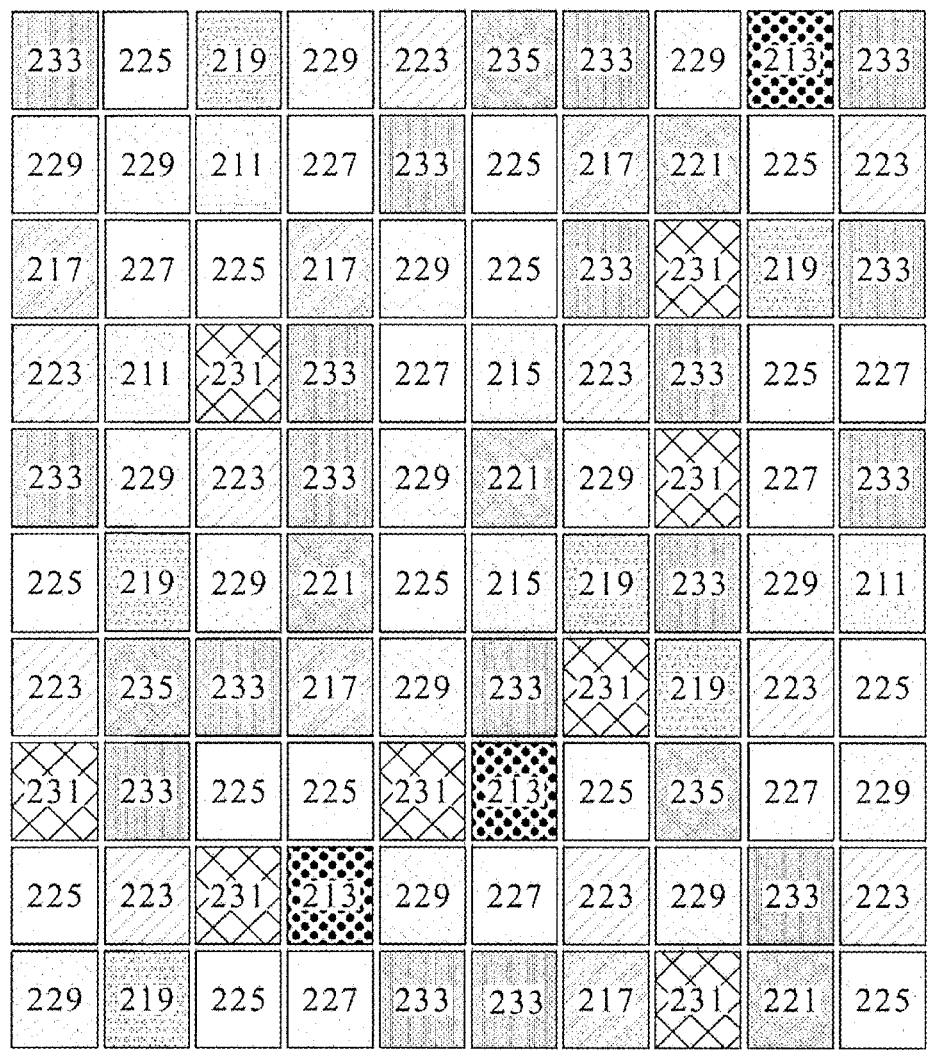
FIG. 33 is a schematic view of the LED array arranged in the mosaic mode of another aspect of the second embodiment of the present invention.
Figure 35:
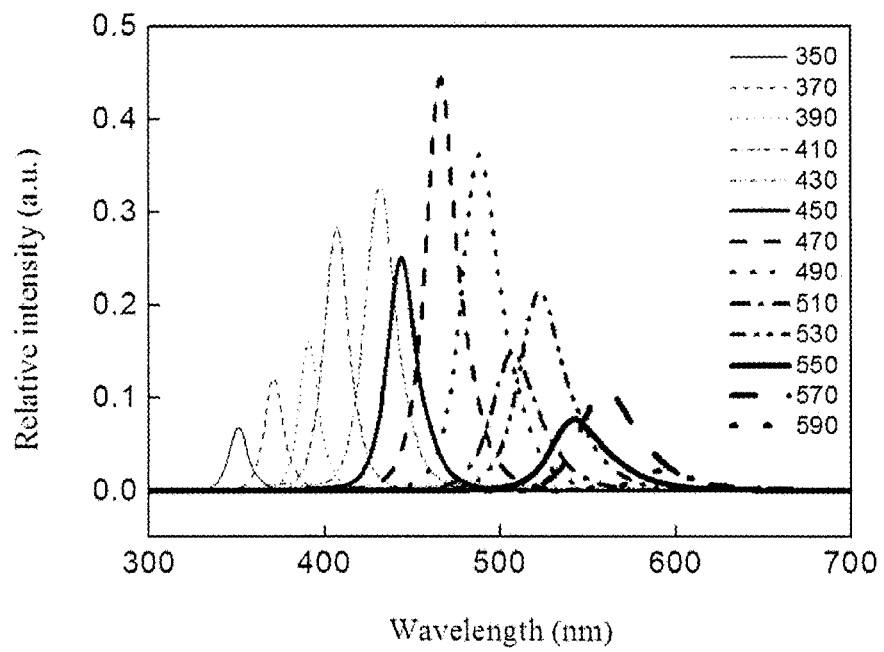
FIG. 35 shows the emission peaks emitted by the LED arrays illustrated in FIG. 33 and FIG. 34.
Figure 36:
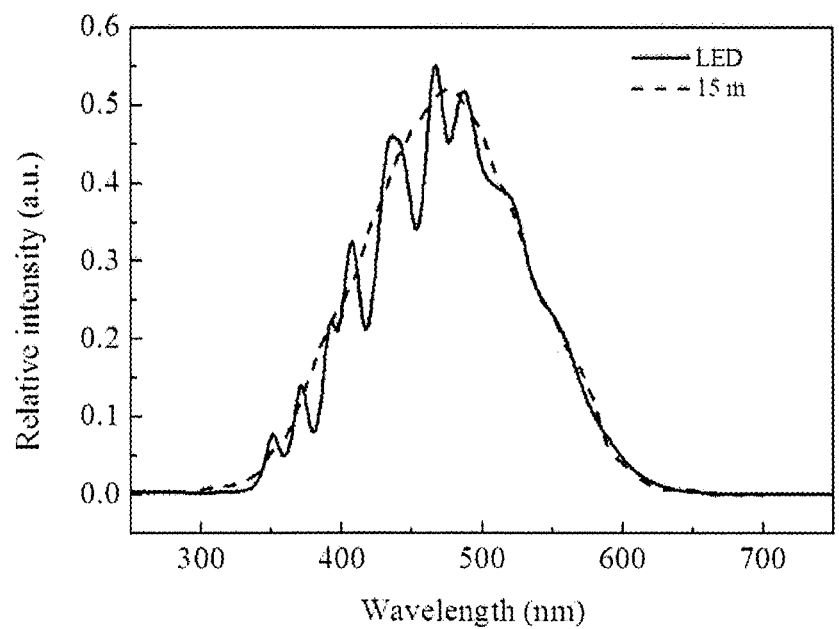
FIG. 36 shows the spectrums of the simulation lights emitted by the LED arrays illustrated in FIG. 33 and FIG. 34 and the sunlight 15 meters underwater.

In addition, please refer to FIG. 33, if the white light LED element was not used for the present embodiment, the spectrum of sunlight 15 meters underwater may be simulated by using three 350 nm LED elements 211, three 370 nm LED elements 213, two 390 nm LED elements 215, five 410 nm LED elements 217, six 430 nm LED elements 219, four 450 nm LED elements 221, ten 470 nm LED elements 223, fifteen 490 nm LED elements 225, eight 510 nm LED elements 227, fifteen 530 nm LED elements 229, eight 550 nm LED elements 231, eighteen 570 nm LED elements 233, and three 590 nm LED elements 235. Similarly, the present embodiment is not limited to the mosaic mode arrangement, and may be arranged in the straight mode as illustrated in FIG. 34, but not limited thereto. Accordingly, after the LED array of the present embodiment was driven, the emission peaks (the maximum peak intensity of the emission peaks in the first and the third emission groups were 0.73 and 0.26) shown in the following table 9 and FIG. 35 may be emitted by those light emitting elements for mixing the simulating spectrum shown in FIG. 36.

TABLE 9 simulation of 15 meters underwater

| | Emission peak ($\lambda_{max}$) | Peak intensity ratio |
|---|---|---|
| First group of emission peaks (300 nm ≤ $\lambda_{max}$ < 450 nm) | 350 nm | 0.14 |
| | 370 nm | 0.28 |
| | 390 nm | 0.36 |
| | 410 nm | 0.62 |
| | 430 nm | 0.73 |

TABLE 9-continued simulation of 15 meters underwater

| | Emission peak ($\lambda_{max}$) | Peak intensity ratio |
|---|---|---|
| Second group of emission peaks (450 nm ≤ $\lambda_{max}$ < 550 nm) | 450 nm | 0.56 |
| | 470 nm | 1.00 |
| | 490 nm | 0.81 |
| | 510 nm | 0.46 |
| | 530 nm | 0.17 |
| Third group of emission peaks (550 nm ≤ $\lambda_{max}$ < 600 nm) | 550 nm | 0.16 |
| | 570 nm | 0.26 |
| | 590 nm | 0.05 |

Figure 37:
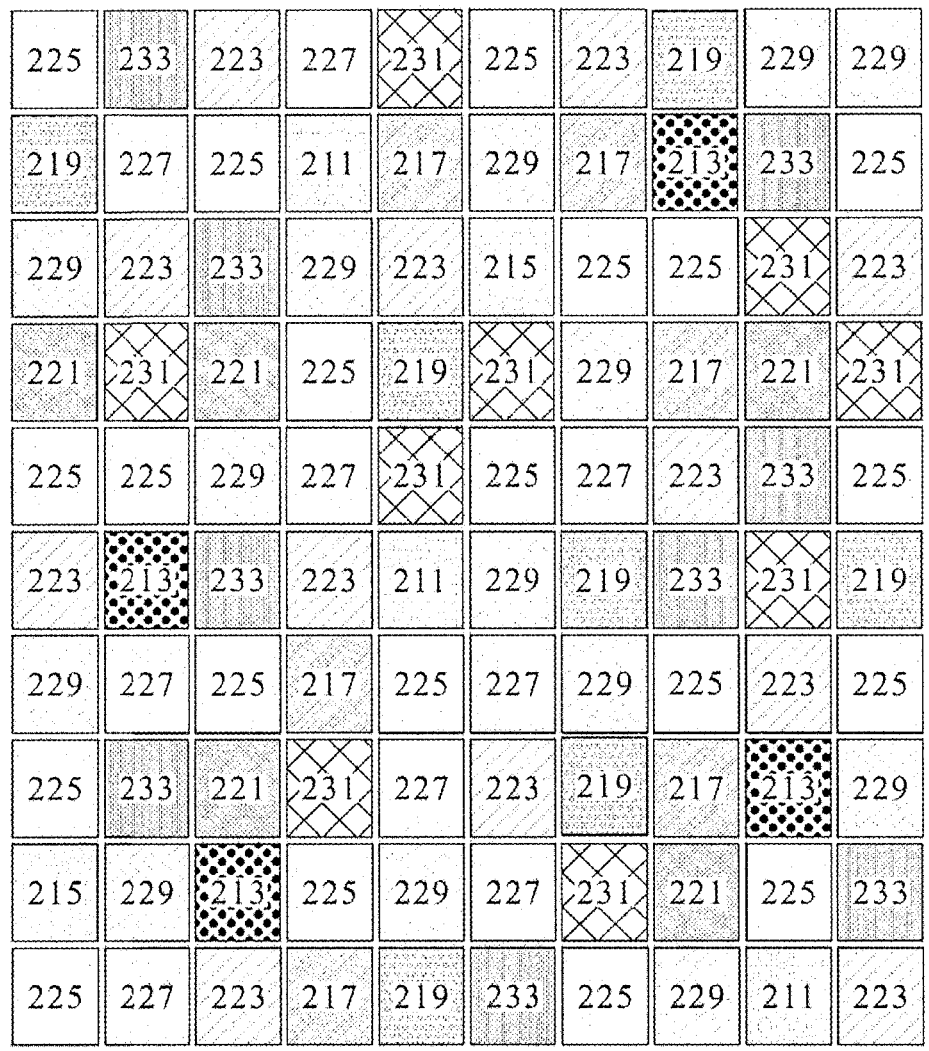
FIG. 37 is a schematic view of the LED array arranged in the mosaic mode of another aspect of the second embodiment of the present invention.
Figure 38:
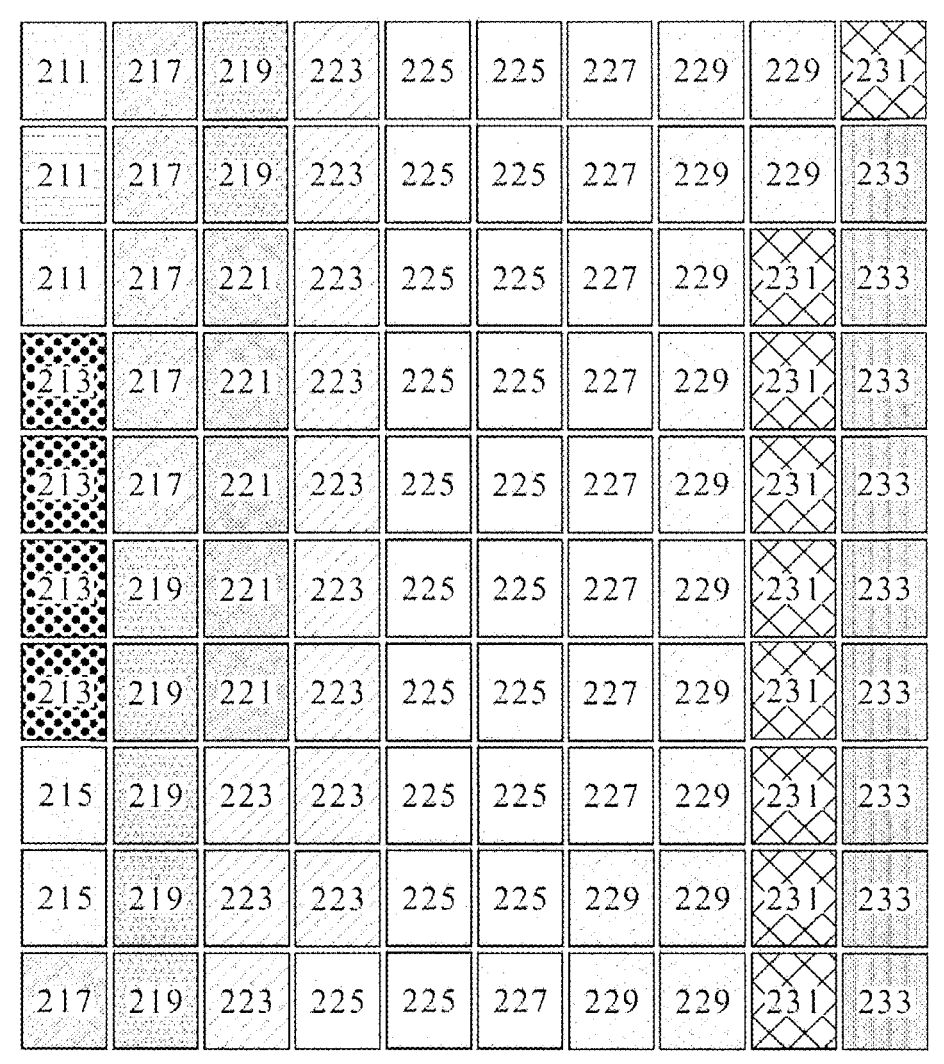
Figure 39:
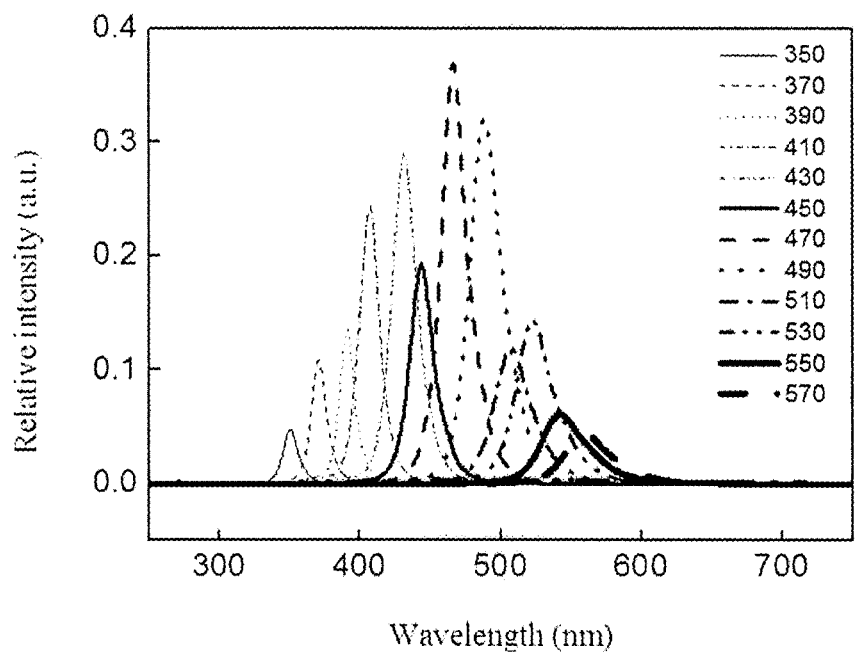
FIG. 39 shows the emission peaks emitted by the LED arrays illustrated in FIG. 37 and FIG. 38.
Figure 40:
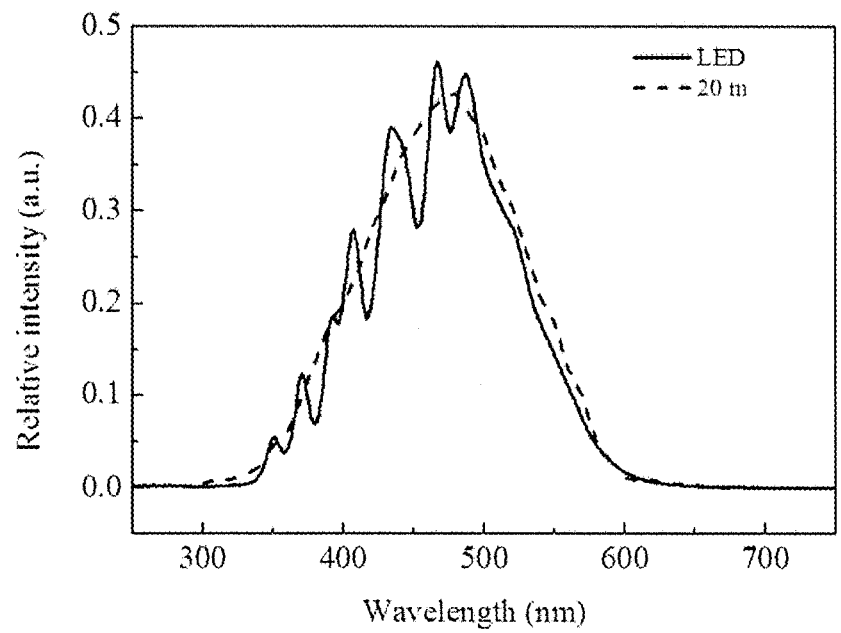
FIG. 40 shows the spectrums of the simulation lights emitted by the LED arrays illustrated in FIG. 37 and FIG. 38 and the sunlight 20 meters underwater.

The simulation of the spectrum of sunlight 20 meters underwater is exemplified. As illustrated in FIG. 37, three 350 nm LED elements 211, four 370 nm LED elements 213, two 390 nm LED elements 215, six 410 nm LED elements 217, seven 430 nm LED elements 219, five 450 nm LED elements 221, twelve 470 nm LED elements 223, twenty 490 nm LED elements 225, nine 510 nm LED elements 227, fourteen 530 nm LED elements 229, nine 550 nm LED elements 231, and nine 570 nm LED elements 233 were applied in the present embodiment, wherein the lights with multi-wavelength were emitted from the LED chips directly. Similarly, the present embodiment is not limited to the mosaic mode arrangement, and may be arranged in the straight mode as illustrated in FIG. 38, but not limited thereto. Accordingly, after the LED array of the present embodiment was driven, the emission peaks (the maximum peak intensity of the emission peaks in the first and the third emission groups were 0.78 and 0.17) shown in the following table 10 and FIG. 39 may be emitted by those light emitting elements for mixing the simulating spectrum shown in FIG. 40.

TABLE 10 simulation of 20 meters underwater

| | Emission peak ($\lambda_{max}$) | Peak intensity ratio |
|---|---|---|
| First group of emission peaks (300 nm ≤ $\lambda_{max}$ < 450 nm) | 350 nm | 0.13 |
| | 370 nm | 0.29 |
| | 390 nm | 0.36 |
| | 410 nm | 0.66 |
| | 430 nm | 0.78 |
| Second group of emission peaks (450 nm ≤ $\lambda_{max}$ < 550 nm) | 450 nm | 0.51 |
| | 470 nm | 1.00 |
| | 490 nm | 0.87 |
| | 510 nm | 0.32 |
| | 530 nm | 0.39 |
| Third group of emission peaks (550 nm ≤ $\lambda_{max}$ < 600 nm) | 550 nm | 0.17 |
| | 570 nm | 0.12 |

Figure 41:
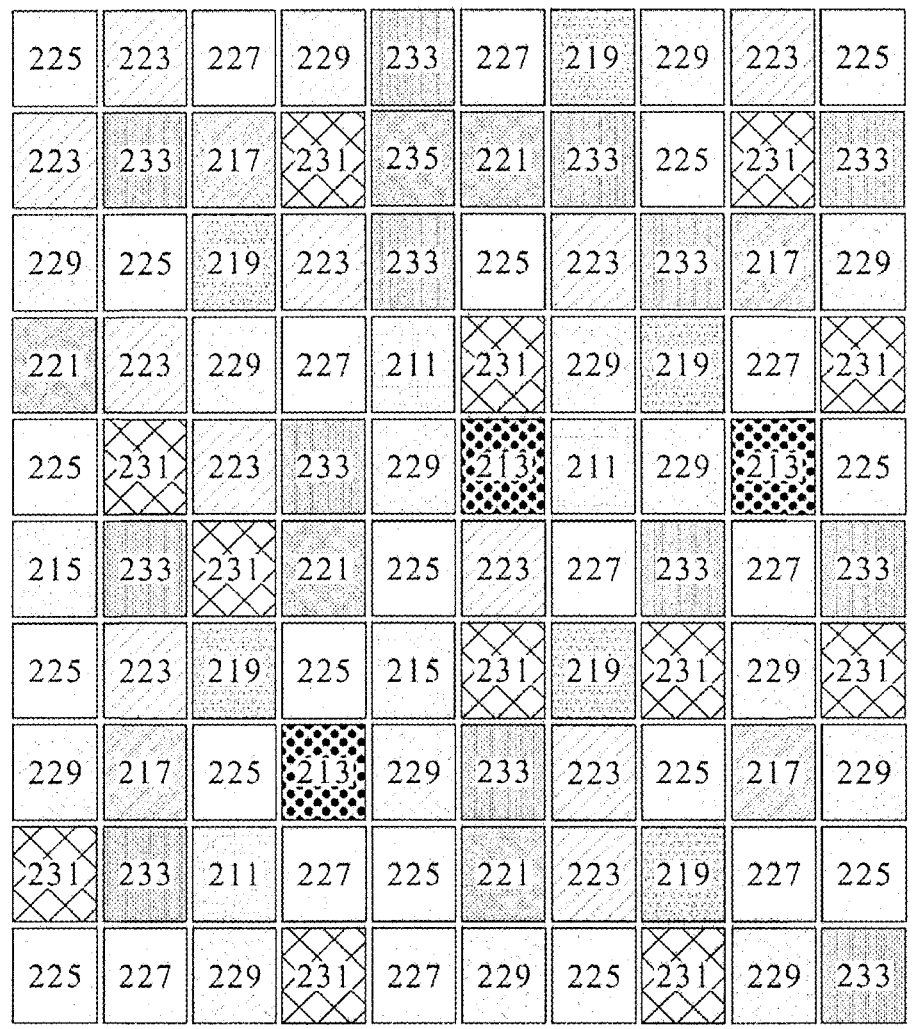
FIG. 41 is a schematic view of the LED array arranged in the mosaic mode of another aspect of the second embodiment of the present invention.
Figure 43:
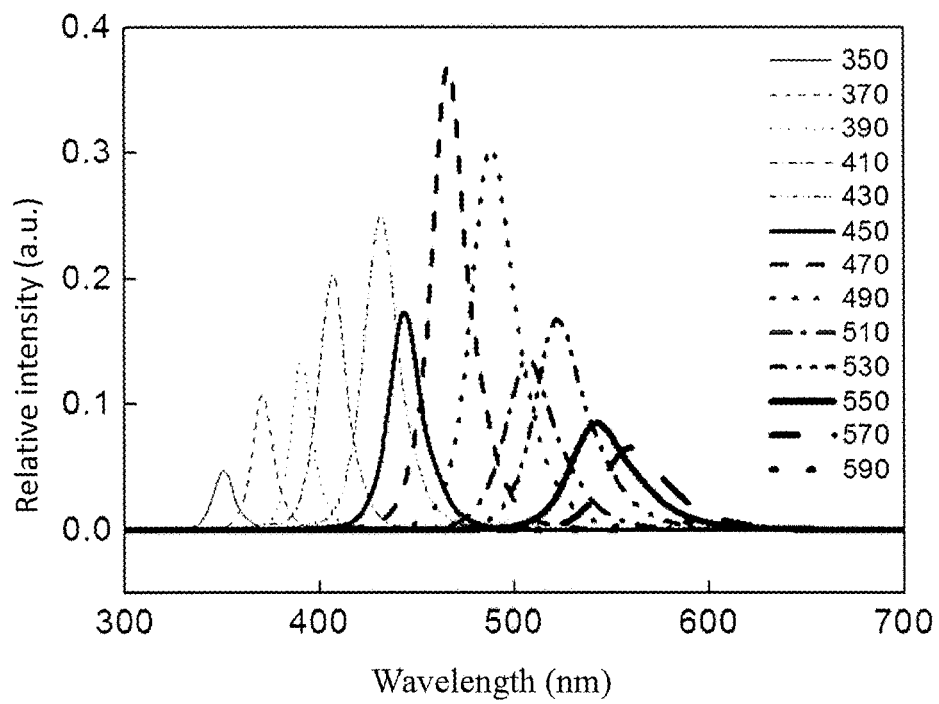
FIG. 43 shows the emission peaks emitted by the LED arrays illustrated in FIG. 41 and FIG. 42.
Figure 44:
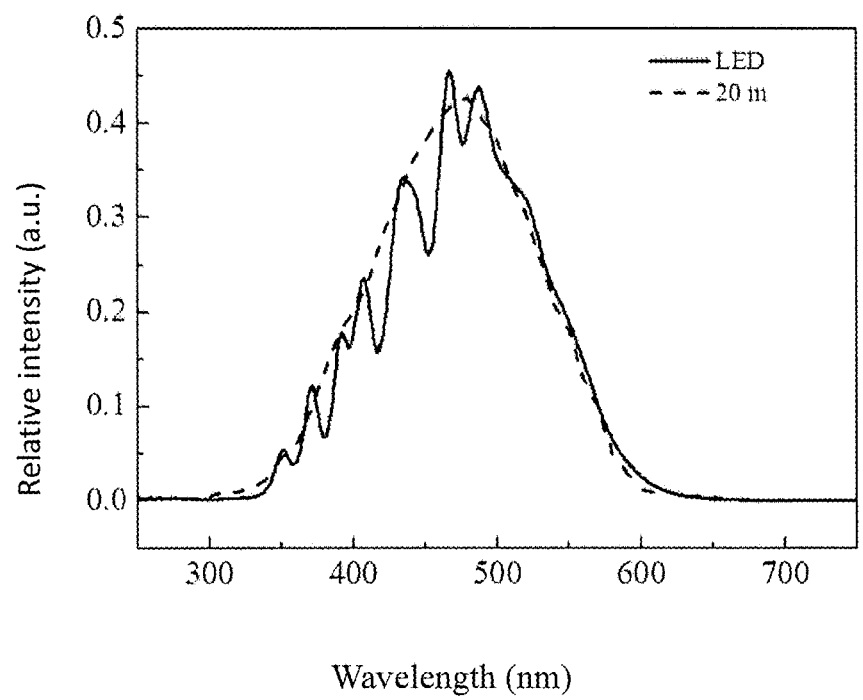
FIG. 44 shows the spectrums of the simulation lights emitted by the LED arrays illustrated in FIG. 41 and FIG. 42 and the sunlight 20 meters underwater.

In addition, please refer to FIG. 41, if the white light LED element was not used for the present embodiment, the spectrum of sunlight 20 meters underwater may be simulated by using three 350 nm LED elements 211, three 370 nm LED elements 213, two 390 nm LED elements 215, four 410 nm LED elements 217, six 430 nm LED elements 219, four 450 nm LED elements 221, eleven 470 nm LED elements 223, sixteen 490 nm LED elements 225, ten 510 nm LED elements 227, fifteen 530 nm LED elements 229, twelve 550 nm LED elements 231, thirteen 570 nm LED elements 233, and one 590 nm LED element 235. Similarly, the present embodiment is not limited to the mosaic mode arrangement, and may be arranged in the straight mode as illustrated in FIG. 42, but not limited thereto. Accordingly, after the LED array of the present embodiment was driven, the emission peaks (the maximum peak intensity of the emission peaks in the first and the third emission groups were 0.63 and 0.24) shown in the following table 11 and FIG. 43 may be emitted by those light emitting elements for mixing the simulating spectrum shown in FIG. 44.

TABLE 11 simulation of 20 meters underwater

| | Emission peak ($\lambda_{max}$) | Peak intensity ratio |
|---|---|---|
| First group of emission peaks (300 nm ≤ $\lambda_{max}$ < 450 nm) | 350 nm | 0.12 |
| | 370 nm | 0.29 |
| | 390 nm | 0.38 |
| | 410 nm | 0.55 |
| | 430 nm | 0.69 |
| Second group of emission peaks (450 nm ≤ $\lambda_{max}$ < 550 nm) | 450 nm | 0.48 |
| | 470 nm | 1.00 |
| | 490 nm | 0.83 |
| | 510 nm | 0.39 |
| | 530 nm | 0.47 |
| Third group of emission peaks (550 nm ≤ $\lambda_{max}$ < 600 nm) | 550 nm | 0.24 |
| | 570 nm | 0.19 |
| | 590 nm | 0.06 |

Embodiment 3

Figure 45:
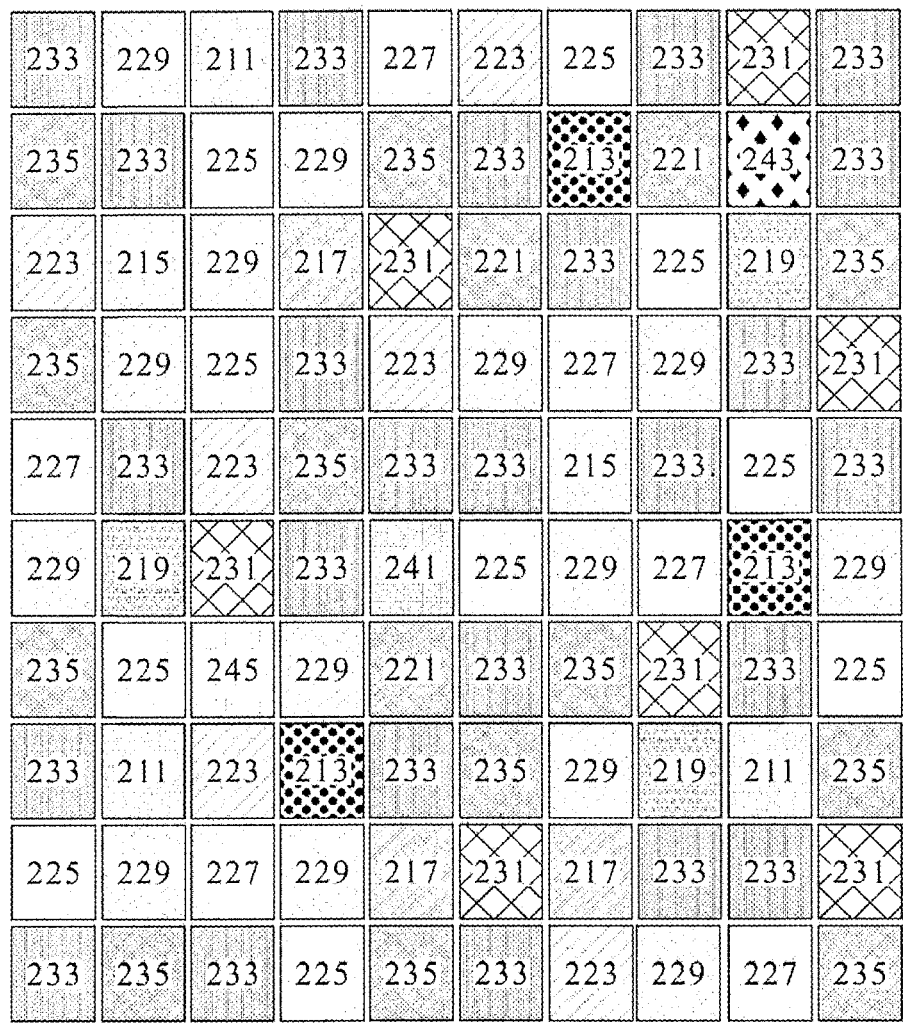
FIG. 45 is a schematic view of the LED array arranged in the mosaic mode of the third embodiment of the present invention.
Figure 46:
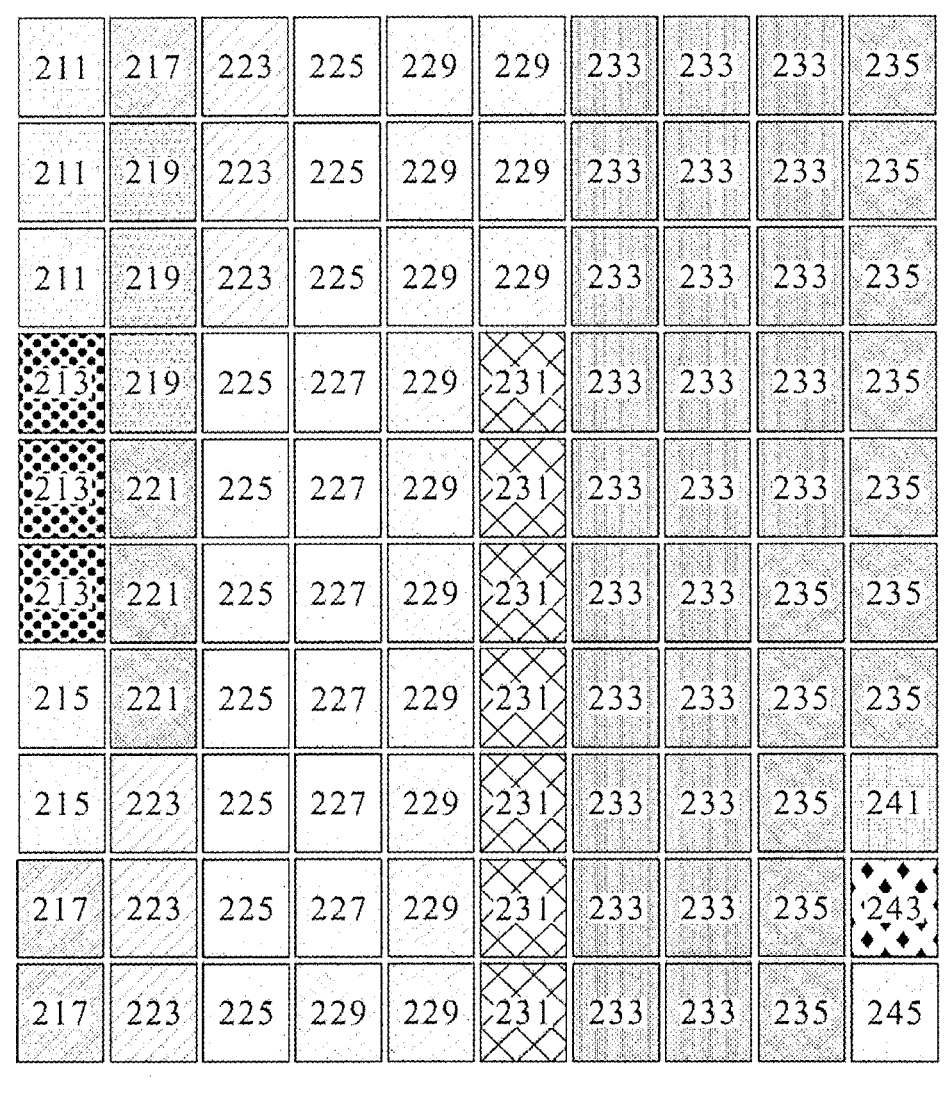
Figure 47:
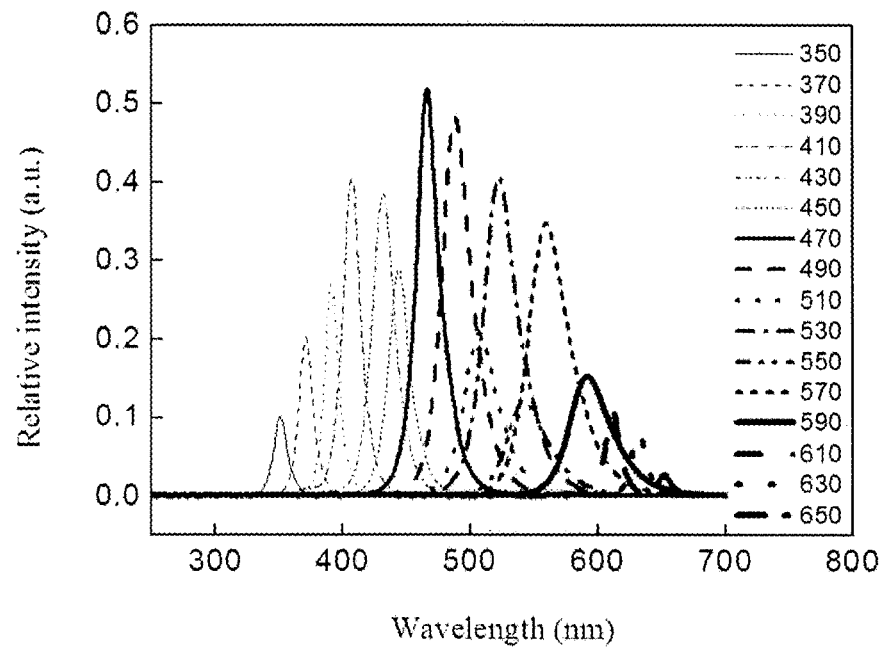
FIG. 47 shows the emission peaks emitted by the LED arrays illustrated in FIG. 45 and FIG. 46.
Figure 48:
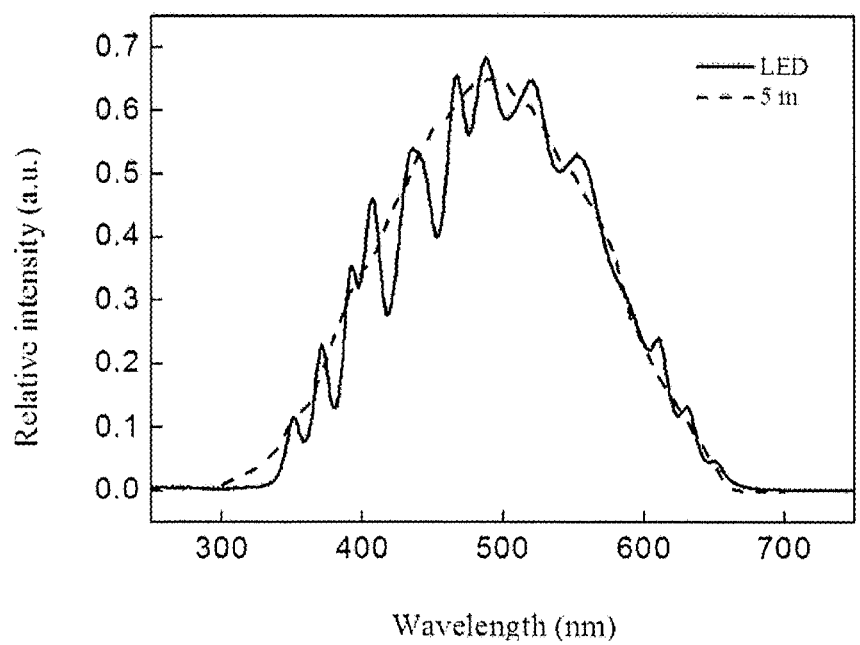
FIG. 48 shows the spectrums of the simulation lights emitted by the LED arrays illustrated in FIG. 45 and FIG. 46 and the sunlight 5 meters underwater.

The present embodiment utilized 10×10 LED array similar to the aforementioned embodiment 2 to mix and match the spectrum, but the LED array of the present embodiment further provided a fourth group of emission peaks. The simulation of the spectrum of sunlight 5 meters underwater is exemplified. As illustrated in FIG. 45, three 350 nm LED elements 211, three 370 nm LED elements 213, two 390 nm LED elements 215, three 410 nm LED elements 217, three 430 nm LED elements 219, three 450 nm LED elements 221, six 470 nm LED elements 223, ten 490 nm LED elements 225, six 510 nm LED elements 227, fourteen 530 nm LED elements 229, seven 550 nm LED elements 231, twenty-five 570 nm LED elements 233, twelve 590 nm LED elements 235, one 610 nm LED element 241, one 630 nm LED element 243, and one 650 nm LED element 245 were applied in the present embodiment, wherein the lights with multi-wavelength were emitted from the LED chips directly. Similarly, the present embodiment is not limited to the mosaic mode arrangement, and may be arranged in the straight mode as illustrated in FIG. 46, but not limited thereto. Accordingly, after the LED array of the present embodiment was driven, the emission peaks (the maximum peak intensity of the emission peaks in the first, the third, and the fourth emission groups were 0.77, 0.67, and 0.21) shown by the following table 12 and FIG. 47 may be emitted by those light emitting elements for mixing the simulating spectrum shown in FIG. 48. Herein, the emission peaks ranging in 510 nm to 700 nm may be provided by the fluorescence powder having emission peaks of 510 nm to 700 nm.

TABLE 12 simulation of 5 meters underwater

| | Emission peak ($\lambda_{max}$) | Peak intensity ratio |
|---|---|---|
| First group of emission peaks (300 nm ≤ $\lambda_{max}$ < 450 nm) | 350 nm | 0.19 |
| | 370 nm | 0.39 |
| | 390 nm | 0.51 |
| | 410 nm | 0.77 |
| | 430 nm | 0.74 |

TABLE 12-continued simulation of 5 meters underwater

| | Emission peak ($\lambda_{max}$) | Peak intensity ratio |
|---|---|---|
| Second group of emission peaks (450 nm ≤ $\lambda_{max}$ < 550 nm) | 450 nm | 0.55 |
| | 470 nm | 1.00 |
| | 490 nm | 0.93 |
| | 510 nm | 0.37 |
| | 530 nm | 0.78 |
| Third group of emission peaks (550 nm ≤ $\lambda_{max}$ < 600 nm) | 550 nm | 0.24 |
| | 570 nm | 0.67 |
| | 590 nm | 0.29 |
| Fourth group of emission peaks (600 nm ≤ $\lambda_{max}$ < 700 nm) | 610 nm | 0.21 |
| | 630 nm | 0.16 |
| | 650 nm | 0.06 |

In summary, the light source module of the present invention may simulate the spectrum of sunlight underwater to provide the light of natural living environment for the aquatic organisms to increase the growing rate thereof. Also, the problems of the overheated environment caused by the heat radiation may be prevented; therefore, the light source module of the present invention is suitable to serve as a plant light for growing aquatic plants and provides the light needed for growing other aquatic organisms.

Although the present invention has been explained in relation to its preferred embodiment, it is to be understood that many other possible modifications and variations can be made without departing from the spirit and scope of the invention as hereinafter claimed.

What is claimed is:

1. A light source module, comprising:
a wiring board; and
an LED array electrically connected to the wiring board which is driven to emit a first group of emission peaks in 300 nm≤λmax<450 nm, a second group of emission peaks in 450 nm≤λmax<550 nm, and a third group of emission peaks in 550 nm≤λmax<600 nm, wherein the LED array includes a plurality of LED elements for emitting the first group of emission peaks, the second group of emission peaks and the third group of emission peaks, respectively; and a peak intensity Ia of each emission peak in the first group is in a range of 0<Ia≤0.9 and the peak intensity Ib of each emission peak in the third group is in a range of 0<Ib≤0.9 and at least three of the emission peaks in the second group have peak intensity in a range of 0.28 to 0.94 when a maximum peak intensity of the emission peaks in the second group is taken as 1.0;
wherein the LED array is selected from the group consisting of:
an array including at least two 390 nm LED elements, at least three 410 nm LED elements, at least three 430 nm LED elements for emitting the first group of emission peaks; at least one 450 nm LED element, at least six 470 nm LED elements at least eight 490 nm LED elements, at least seven 510 nm LED elements, at least nine 530 nm LED elements for emitting the second group of emission peaks; and at least seven 550 nm LED elements, and three 570 nm LED elements for emitting the third group of emission peaks;
an array including at least one 390 nm LED element, least two 410 nm LED elements, at least two 430 nm LED elements for emitting the first group of emission peaks; at least three 450 nm LED elements, at least four 470 nm LED elements, at least six 490 nm LED elements, at least five 510 nm LED elements, at least six 530 nm LED elements for emitting the second group of emission peaks; and at least eight 550 nm LED elements, and twelve 570 nm LED elements for emitting the third group of emission peaks;
an array including at least one 390 nm LED element, at least three 410 nm LED elements, and at least three 430 nm LED elements for emitting the first group of emission peaks; at least three 450 nm LED elements, at least six 470 nm LED elements, at least eight 490 nm LED elements, at least six 510 nm LED elements, and at least six 530 nm LED elements for emitting the second group of emission peaks; and at least six 550 nm LED elements, and at least seven 570 nm LED elements for emitting the third group of emission peaks; and
an array including at least one 390 nm LED element, at least two 410 nm LED elements, and at least four 430 nm LED elements for emitting the first group of emission peaks; at least two 450 nm LED elements, at least six 470 nm LED elements, at least nine 490 nm LED elements, at least seven 510 nm LED elements, and at least six 530 nm LED elements for emitting the second group of emission peaks; and at least six 550 nm LED elements, and at least six 570 nm LED elements for emitting the third group of emission peaks.

2. The light source module as claimed in claim 1, wherein a maximum peak intensity of the first group of emission peaks is in a range of 0.5 to 0.9, and a maximum peak intensity of the third group of emission peaks is in a range of 0.1 to 0.8.

3. The light source module as claimed in claim 2, wherein the maximum peak intensity of the first group of emission peaks is in a range of 0.68 to 0.80.

4. The light source module as claimed in claim 2, wherein at least three of the emission peaks in the first group have peak intensity in a range of 0.12 to 0.80.

5. The light source module as claimed in claim 4, wherein at least two of the emission peaks in the first group have peak intensity in a range of 0.21 to 0.80.

6. The light source module as claimed in claim 1, wherein these LED elements are arranged in mosaic mode or straight mode.

7. The light source module as claimed in claim 1, wherein each of the LED elements includes a plurality of LED chips, and the emission peaks are provided by the LED chips with different wavelengths.

8. The light source module as claimed in claim 1, wherein at least one of the LED elements includes an LED excitation source and a fluorescence material layer on the LED excitation source, and others of the LED elements each include an LED chip, and the emission peaks are provided by the LED chips with different wavelengths and the fluorescence material layer on the LED excitation source, wherein the light emitted by the fluorescence material layer is in a range of 510 nm≤λmax<600 nm.

9. The light source module as claimed in claim 8, wherein the excitation light emitted from the LED excitation source is in a range of 200 nm≤λmax<490 nm.

10. The light source module as claimed in claim 8, wherein a waveband of the light emitted by the fluorescence material layer is further in a range of 620 nm to 780 nm.

11. The light source module as claimed in claim 8, wherein the light with a CIE1931 color coordinate of 0.1≤x≤0.65 and 0.35≤y≤0.85 is emitted by the fluorescence material layer.

12. The light source module as claimed in claim 1, wherein a fourth group of emission peaks is further emitted when the LED array is driven, wherein the fourth group of emission peaks includes at least one emission peak in 600 nm≤λmax<700 nm, and the LED array further includes at least one additional LED element for emitting the emission peak in 600 nm≤λmax<700 nm.

13. The light source module as claimed in claim 12, wherein the additional LED element includes an LED chip or includes an LED excitation source and a fluorescence material layer on the LED excitation source, and the at least one emission peak of the fourth group of emission peaks is provided by the LED chip or the fluorescence material layer on the LED excitation source.

14. The light source module as claimed in claim 1, wherein the LED elements are surface mount LED elements, wherein the surface mount LED elements are arranged on the wiring board.

15. The light source module as claimed in claim 1, wherein at least two of the emission peaks in the second group have peak intensity in a range of 0.41 to 0.89.

16. The light source module as claimed in claim 1, wherein any four adjacent ones of the LED elements provide at least two emission peaks with different peak wavelengths to form a partial 2×2 sub-array of mixed light.

17. The light source module as claimed in claim 1, wherein each two adjacent ones of the emission peaks in the first group, the second group and the third group have wavelength difference of 20 nm.

* * * * *